United States Patent
Irizarry

(10) Patent No.: US 10,546,243 B1
(45) Date of Patent: Jan. 28, 2020

(54) PREDICTING PARTICLE SIZE DISTRIBUTION AND PARTICLE MORPHOLOGY

(71) Applicant: Merck Sharp & Dohme Corp., Rahway, NJ (US)

(72) Inventor: Roberto Irizarry, Wayne, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/126,048

(22) Filed: Sep. 10, 2018

(51) Int. Cl.
| G06F 15/18 | (2006.01) |
| G06N 7/00 | (2006.01) |
| G01N 15/02 | (2006.01) |
| G06N 20/00 | (2019.01) |

(52) U.S. Cl.
CPC ......... G06N 7/005 (2013.01); G01N 15/0205 (2013.01); G06N 20/00 (2019.01)

(58) Field of Classification Search
CPC ............................ G01N 15/0205; G06N 7/005
See application file for complete search history.

(56) References Cited

U.S. PATENT DOCUMENTS

| 8,374,801 B2 * | 2/2013 | Fuhrman | G01J 3/02 |
| | | | 702/28 |
| 10,088,404 B2 * | 10/2018 | Dietrich | G01N 15/0205 |
| 2007/0122349 A1 * | 5/2007 | Wachtel | G01N 15/0205 |
| | | | 424/45 |
| 2008/0068379 A1 * | 3/2008 | Larsen | G06K 9/0014 |
| | | | 345/427 |
| 2014/0146314 A1 * | 5/2014 | Ronaes | G01N 15/1459 |
| | | | 356/336 |

OTHER PUBLICATIONS

"Data-driven model and model paradigm to predict 1D and 2D particle size distribution from measured chord-length distribution" Irizarry et al (Year: 2017).*
"Obtaining Particle Size Distribution from Chord Length Measurements" Mingzhong Li, Derek Wilkinson, Kumar Patchigolla (Year: 2006).*
"Models for Estimating Soil Particle-Size Distributions" Hwang et al (Year: 2002).*

(Continued)

Primary Examiner — Luis A Sitiriche
(74) Attorney, Agent, or Firm — Fenwick & West LLP

(57) ABSTRACT

This disclosure relates to a method for estimating a particle size distribution (PSD) and a morphology for a set of particles. A computer system receives a plurality of chord length distributions (CLDs) of different types for a set of particles. The computer system then estimates a morphology for the set of particles based on the plurality of received CLDs. The computer system also identifies a plurality of descriptors of the plurality of CLDs for the set of particles based on the plurality of received CLDs. The computer system then estimates metrics for the PSD for the set of particles based on the plurality of identified CLD descriptors. Based on the estimated PSD metrics for the set of particles, the computer system generates an estimate of the PSD for the set of particles. Finally, the computer system outputs the estimated morphology and the estimated PSD for the set of particles.

20 Claims, 22 Drawing Sheets

(56) References Cited

OTHER PUBLICATIONS

"Chord length distributions measurements during crystallization and agglomeration of gas hydrate in a water-in-oil emulstion: Simulation and experimentation" Hung Le Ba et al (Year: 2010).*
Irizarry, R. et al., "Data-Driven Model and Model Paradigm to Predict 1D and 2D Particle Size Distribution from Measured Chord-Length Distribution," Chemical Engineering Science 164, Feb. 8, 2017, pp. 202-218.

* cited by examiner

PREDICTING PARTICLE SIZE DISTRIBUTION AND PARTICLE MORPHOLOGY

TECHNICAL FIELD

The present disclosure generally relates to predicting a particle size distribution (PSD) and a particle morphology for a set of particles, based on a chord length distribution (CLD) for the set of particles. In particular, the present disclosure relates to predicting a PSD and a particle morphology for a set of particles, based on a plurality of CLDs for the set of particles, each CLD comprising a different type of CLD.

BACKGROUND

In many existing applications, a chord length distribution (CLD) is used for in-line monitoring to depict a size distribution for a set of particles. However, a CLD may be an inaccurate and an imprecise measure of particle size. First, a CLD can be an inaccurate measure of particle size because measurement tools frequently inaccurately measure a particle's chord length. For example, a chord length for a first particle may be inaccurately measured as a sum of the chord length of the first particle and a chord length of a second particle located near the first particle. In addition to CLD being an inaccurate measure of particle size, CLD can also be an imprecise measure of particle size because, for each particle, a nearly infinite number of different chord lengths may be identified. Specifically, a nearly infinite number of different chord lengths may be identified for a given particle depending upon an orientation of the particle with respect to the device performing the chord length measurement. This variability in chord length for a single particle is even further compounded for a set of particles. As a result of this variability in CLD for a set of particles, CLD is an imprecise measure of particle size for a set of particles.

As a result of this inaccuracy and imprecision of a CLD as a measurement of particle size for a set of particles, it cannot easily be correlated with particle size. Specifically, one alternative to using a CLD as a measurement of particle size for a set of particles is use of a particle size distribution (PSD). In some embodiments, a PSD for a set of particles can be generated based on a CLD for the set of particles. However, existing models that are configured to generate a PSD based on a CLD are often specific to a particular type of CLD and to a specific particle morphology. In other words, an existing model that is configured to generate a PSD based on a CLD may only be able to generate a PSD based on a particular type of CLD and a particular particle morphology on which the model was previously trained and validated. There are a plurality of types of CLDs and large variation in particle morphologies in many systems of interest. Therefore, to be capable of generating a PSD for a set of particles based on a CLD of any of the plurality of CLD types, existing methods require a plurality of different models to be trained and validated. Most importantly, a different model is required for each different particle morphology.

Many particle systems exhibit large deviations in morphology during in-line CLD monitoring when morphological changes occur. Existing models that predict PSD from an in-line CLD do not work well when these morphological changes occur. These existing models are incapable of identifying a morphology for the set of particles.

SUMMARY

The present disclosure relates generally to systems, devices, and methods for estimating a particle size distribution (PSD) and a morphology for a set of particles.

In one aspect, the disclosure provides a method for estimating a PSD and a morphology for a set of particles. The method includes receiving, from a probe, at a computer system, a plurality of chord length distributions (CLDs) for a set of particles. Each CLD of the plurality of CLDs comprises a different type of CLD. A plurality of types of CLDs exist. A CLD type can depend on one or more of the following factors: digital processing of the data received from the probe and weighting of the data received from the probe. For example, the digital processing of the data received from the probe can be coarse. As another example, the data received from the probe can be multiplied by its square weight. As another example, the data received from the probe may not be weighted at all. Therefore any number of types of CLDs may exist. In some embodiments, the plurality of CLDs received from the probe include four CLDs, each CLD comprising one of the four types of CLDs. In alternative embodiments, the plurality of CLDs received from the probe can include any number of different CLD types.

The computer system estimates a morphology for the set of particles using a morphology estimation model, based on the received plurality of CLDs. The computer system also identifies a plurality of descriptors of the plurality of CLDs for the set of particles using a descriptor identifier, based on the plurality of CLDs for the set of particles. The computer system estimates metrics for the PSD for the set of particles, using a statistical model, based on the plurality of identified CLD descriptors. Based on the estimated PSD metrics for the set of particles, the computer system uses a parameterized PSD model to generate an estimate of the PSD for the set of particles. Specifically, the computer system generates an estimate of the PSD for the set of particles by applying a parameterized PSD model to the estimated PSD metrics for the set of particles. Finally, the computer system outputs the estimated morphology for the set of particles, and the estimated PSD for the set of particles.

Turning first to the morphology estimation model, in some embodiments, the morphology estimation model includes one of a fuzzy classification model, a neuro-fuzzy classification model, a random forest model, a decision tree, a clustering algorithm, a neural network, a multi-class logistic regression model, a deep learning model, and a Bayesian model. In addition to estimating the morphology for the set of particles based on the plurality of received CLDs, in some embodiments the estimated morphology for the set of particles is further based on one or more of an in-line particle concentration for the set of particles and an in-line particle video for the set of particles. In further embodiments, the estimated morphology for the set of particles may be based on the identified plurality of descriptors of the plurality of CLDs for the set of particles.

The morphology estimate generated by the morphology estimation model may comprise one of a discrete morphology estimate, a continuous morphology estimate, and both a discrete and a continuous morphology estimate. A discrete morphology estimate is an estimate of a single, most probable morphology for a set of particles. An example of a discrete estimated morphology is a morphology B. A continuous morphology estimate is an estimate of a plurality of estimated morphologies for the set of particles, each estimated morphology of the plurality of estimated morphologies associated with a percentage or a fraction that represents an estimated probability of that morphology occurring in the set of particles. An example of a continuous morphology estimate for a set of particles is a morphology A associated with a 10% probability of occurring in the set of particles, a morphology B associated with a 20% probability of occurring in the set of particles, and a morphology C associated with a 70% probability of occurring in the set of particles. Finally, both a discrete and a continuous morphology estimate for a set of particles is an estimate of a plurality of most probable morphologies for the set of particles, each estimated morphology in the plurality associated with a percentage or a fraction that represents an estimated probability of that morphology occurring in the set of particles, as well as a single most probable morphology estimate that is identified based on the continuous morphology estimate. For example, a discrete morphology estimate identified for the example continuous morphology estimate described above would be the morphology C, because the morphology C is associated with the greatest probability of occurring in the set of particles.

In certain embodiments, the estimated particle size distribution for the set of particles is further based on the estimated morphology for the set of particles. In such embodiments in which the estimated particle size distribution for the set of particles is further based on the estimated morphology for the set of particles, the estimated morphology for the set of particles may comprise a discrete or a continuous morphology estimate.

Turning next to the descriptor identifier, in some embodiments, the plurality of descriptors of the plurality of CLDs for the set of particles includes one or more of moments of the plurality of CLDs and a percentage of particles in the set of particles with a particle size below an average particle size. In another embodiment, a geometric model can be used to generate moments of geometric model PSDs. In another embodiment, unsupervised learning can be used with PCA and or auto-encoders to compress the plurality of CLD into a small set of descriptors. Furthermore, in another embodiment, partial least squares, neural networks and deep learning can be used to extract a small set of descriptors from the plurality of CLDs.

Turning next to the statistical model, in some embodiments, the statistical model may be a regression model that is configured to perform regression analysis. Some examples of the statistical model includes a regression model, a sparse regression model, a neural network, a deep learning model, and a partial least squares model. Additionally, in some embodiments, the estimated metrics for the PSD for the set of particles are further based on a slurry concentration of the set of particles. Furthermore, the estimated metrics for the PSD for the set of particles may be further based on a morphology fraction for each morphology of the set of particles.

Finally, turning to the parameterized PSD model, in certain embodiments, the parameterized PSD model may be a parameterized generating function, a neural network model, a multi-class logistic regression model, or a deep learning model.

In some embodiments, one or more of the morphology estimation model, the descriptor identifier, the statistical model, and the parameterized PSD model are trained prior to being used as described above. Specifically, in some embodiments, prior to estimating the morphology for the set of particles, the morphology estimation model is trained using a training dataset. The training dataset may include a plurality of training samples, each training sample associated with a training set of particles and identifying a plurality of CLDs of different types and a morphology for the training set of particles. In some embodiments, the training samples of the training dataset for the morphology estimation model may be associated with training sets of particles with a plurality of different morphologies. In other words, the morphology estimation model may be trained to estimate a morphology for a set of particles of any morphology. In embodiments in which an estimated morphology for a set of particles is further based on one or more of an in-line particle concentration for the set of particles and an in-line particle video for the set of particles, each training sample of the training dataset for the morphology estimation model can further include one or more of an in-line particle concentration for the set of particles and an in-line particle video for the training set of particles.

Similarly, in some embodiments, prior to estimating the plurality of descriptors of the plurality of CLDs for the set of particles, the descriptor identifier is trained using a training dataset. The training dataset may include a plurality of training samples, each training sample associated with a training set of particles and including a plurality of CLDs of different types and a plurality of descriptors of the plurality of CLDs for the training set of particles. In some embodiments, the training samples of the training dataset for the descriptor identifier may be associated with training sets of particles with a plurality of different morphologies. In other words, the descriptor identifier may be trained to estimate a plurality of CLD descriptors for a plurality of CLDs for a set of particles of any morphology.

Like the morphology estimation model and the descriptor identifier, in some embodiments the statistical model can also be trained prior to use. Specifically, prior to estimating the PSD metrics for the set of particles, the statistical model is trained using a training dataset, the training dataset including a plurality of training samples, each training sample of the plurality of training samples associated with a training set of particles and including descriptors of a plurality of CLDs and metrics for a PSD for the training set of particles. In some embodiments, the training samples of the training dataset for the statistical model may be associated with training sets of particles with a plurality of different morphologies. In other words, the statistical model may be trained to estimate PSD metrics for a PSD for a set of particles of any morphology. In embodiments in which estimated metrics for a PSD for a set of particles is further based on a slurry concentration of the set of particles, each training sample of the training dataset for the statistical model can further include a slurry concentration for the training set of particles.

In some embodiments, the parameterized PSD model can also be trained prior to use. Specifically, prior to estimating the PSD for the set of particles, the parameterized PSD model is trained using the training dataset, the training dataset including a plurality of training samples, each training sample of the plurality of training samples associated with a training set of particles and including PSD metrics and a PSD for the training set of particles. In certain embodiments, the training samples of the training dataset for the parameterized PSD model may be associated with training sets of particles with a plurality of different morphologies. In other words, the parameterized PSD model may be trained to estimate a PSD for a set of particles of any morphology.

In embodiments in which the morphology estimation model is trained prior to use, the morphology estimation model includes a function representing a relation between the plurality of CLDs of different types for the set of particles and the estimated morphology for the set of particles, the function is based on the training dataset for the morphology estimation model. Similarly, in embodiments in which the descriptor identifier is trained prior to use, the descriptor identifier includes a function representing a relation between the plurality of CLDs of different types for the set of particles and the plurality of identified descriptors of the plurality of CLDs for the set of particles, the function based on the training dataset for the descriptor identifier. In embodiments in which the statistical model is trained prior to use, the statistical model includes a function representing a relation between the plurality of identified descriptors for the plurality of CLDs for the set of particles and the estimated metrics for the PSD for the set of particles, the function based on the training dataset for the statistical model. Finally, in embodiments in which the parameterized PSD model is trained prior to use, the parameterized PSD model includes a function representing a relation between the estimated metrics for the PSD for the set of particles and the estimated PSD for the set of particles, the function based on the training dataset for the parameterized PSD model.

In certain embodiments of the disclosure, the descriptor identifier, the statistical model, and the parameterized PSD model can include a plurality of descriptor identifiers, statistical models, and parameterized PSD models, respectively. Specifically, in certain embodiments, the descriptor identifier includes a plurality of descriptor identifiers, the statistical model includes a plurality of statistical models, and the parameterized PSD model includes a plurality of parameterized PSD models. In such embodiments, each descriptor identifier of the plurality of descriptor identifiers is associated with a different particle morphology, each statistical model of the plurality of statistical models associated with a different particle morphology, and each parameterized PSD model of the plurality of parameterized PSD models associated with a different particle morphology. In other words, each descriptor identifier is configured to identify CLD descriptors for a set of particles including a different particle morphology, each statistical model is configured to estimate PSD metrics for a set of particles with a different particle morphology, and each parameterized PSD model is configured to generate a PSD estimate for a set of particles with a different particle morphology.

In such embodiments in which each descriptor identifier of the plurality of descriptor identifiers is associated with a different particle morphology, to identify the plurality of descriptors of the plurality of CLDs for the set of particles, the computer system selects a descriptor identifier from the plurality of descriptor identifiers that is associated with the estimated morphology for the set of particles. Similarly, in embodiments in which each statistical model of the plurality of statistical models is associated with a different particle morphology, to estimate the PSD metrics for the PSD for the set of particles, the computer system selects a statistical model from the plurality of statistical models that is associated with the estimated morphology for the set of particles. And in embodiments in which each parameterized PSD model of the plurality of parameterized PSD models is associated with a different particle morphology, to generate the estimated PSD for the set of particles, the computer system selects a parameterized PSD model from the plurality of parameterized PSD models that is associated with the estimated morphology for the set of particles. In some embodiments, the selected descriptor identifier identifies the plurality of descriptors for one chord length distribution of the plurality of chord length distributions and the selected statistical model estimates the metrics for the particle size distribution for the set of particles based on the plurality of descriptors for the one chord length distribution of the plurality of chord length distributions.

In embodiments in which the descriptor identifier includes a plurality of descriptor identifiers, the statistical model includes a plurality of statistical models, and the parameterized PSD model includes a plurality of parameterized PSD models, one or more of the plurality of descriptor identifiers, the plurality of statistical models, and the plurality of parameterized PSD models may be trained prior to being used as described above. Specifically, prior to estimating the plurality of descriptors of the plurality of CLDs of different types for the set of particles, in some embodiments, each descriptor identifier of the plurality of descriptor identifiers is trained using a training dataset including a plurality of training samples, each training sample associated with a training set of particles with the morphology associated with the descriptor identifier and including a plurality of CLDs of different types and a plurality of descriptors of the plurality of CLDs for the training set of particles. In other words, each descriptor identifier of the plurality of descriptor identifiers may be trained to estimate a plurality of CLD descriptors for a plurality of CLDs for a set of particles of a different morphology.

Similarly, prior to estimating the PSD metrics for the PSD for the set of particles, in some embodiments each statistical model of the plurality of statistical models is trained using a training dataset including a plurality of training samples, each training sample associated with a training set of particles with the morphology associated with the statistical model and including descriptors of a plurality of CLDs of different types and PSD metrics for the PSD for the training set of particles. In other words, each statistical model of the plurality of statistical models may be trained to estimate PSD metrics for a PSD of a set of particles of a different morphology. Similarly, prior to generating an estimated PSD for the set of particles, in some embodiments each parameterized PSD model of the plurality of parameterized PSD models is trained using a training dataset including a plurality of training samples, each training sample associated with a training set of particles with the morphology associated with the parameterized PSD model and including PSD metrics and the PSD for the training set of particles. In other words, each parameterized PSD model of the plurality of parameterized PSD models may be trained to estimate a PSD for a set of particles of a different morphology.

In certain embodiments, the method for estimating the PSD and the morphology for the set of particles that is disclosed herein may include additional steps. Specifically, the method may further include the computer system estimating parameters for each of a plurality of population balance models (PBMs) based on the estimated PSD for the set of particles. Each PBM of the plurality of PBMs is associated with a different dominant particle formation mechanism. The computer system then applies each of the plurality of PBMs to the estimated morphology for the set of particles and to the estimated parameters for the PBM to generate a theoretical PSD. The computer system then modifies the estimated parameters for each of the plurality of PBMs to reduce the differences between the theoretical PSD generated by the PBM and the estimated PSD for the set of particles to generate a best PBM for the dominant particle formation mechanism. The computer system then applies each of the best PBMs to the received plurality of CLDs for the set of particles to generate a theoretical PSD. Then the computer system applies a geometric mechanistic model to each of the theoretical PSDs to generate a theoretical CLD. Then the computer system identifies a best fitting PBM from the plurality of PBMs that generates a theoretical CLD that best matches the received plurality of CLDs for the set of particles. The computer system then identifies a dominant particle formation mechanism for the set of particles based on the best fitting PBM. Specifically, the dominant particle formation mechanism identified by the computer system is the dominant particle formation mechanism that is associated with the best fitting PBM. Finally, the computer system outputs the identified dominant particle formation mechanism for the set of particles.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

DETAILED DESCRIPTION

Systems, devices, and methods for estimating a particle size distribution (PSD) and a morphology for a set of particles are provided herein. In some embodiments, the systems include a probe in communication with a computer system that is capable of executing the methods described herein. In some embodiments, the methods described herein include receiving, from a probe, a plurality of chord length distributions (CLDs) for a set of particles, each CLD of the plurality comprising a different type of CLD, estimating a morphology for the set of particles using a morphology estimation model, identifying descriptors for the received CLDs, estimating metrics for the PSD using a statistical model, generating an estimate of the PSD using a parameterized PSD model, and outputting the estimated PSD and the estimated morphology for the set of particles.

Before the disclosed embodiments are described in greater detail, it is to be understood that this disclosure is not limited to particular embodiments described, and as such can, of course, vary. It is also to be understood that the terminology used herein is for the purpose of describing particular embodiments only, and is not intended to be limiting, since the scope of the present disclosure will be limited only by the appended claims.

Below are examples of specific embodiments for carrying out the present disclosure. The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

Unless defined otherwise, all technical and scientific terms used herein have the same meaning as commonly understood by one of ordinary skill in the art to which these disclosed embodiments belong. Although any methods and materials similar or equivalent to those described herein can also be used in the practice or testing of the disclosed embodiments, representative illustrative methods and materials are now described. Any recited method can be carried out in the order of events recited or in any other order which is logically possible.

It is noted that, as used herein and in the appended claims, the singular forms "a," "an," and "the" include plural referents unless the context clearly dictates otherwise.

Overall System Environment

Included in the disclosure are systems, devices, and methods for estimating a particle size distribution (PSD) and a morphology for a set of particles. In some embodiments, such as the embodiment depicted in FIG. 1, the systems include a probe in communication with a computer system.

Figure 1:
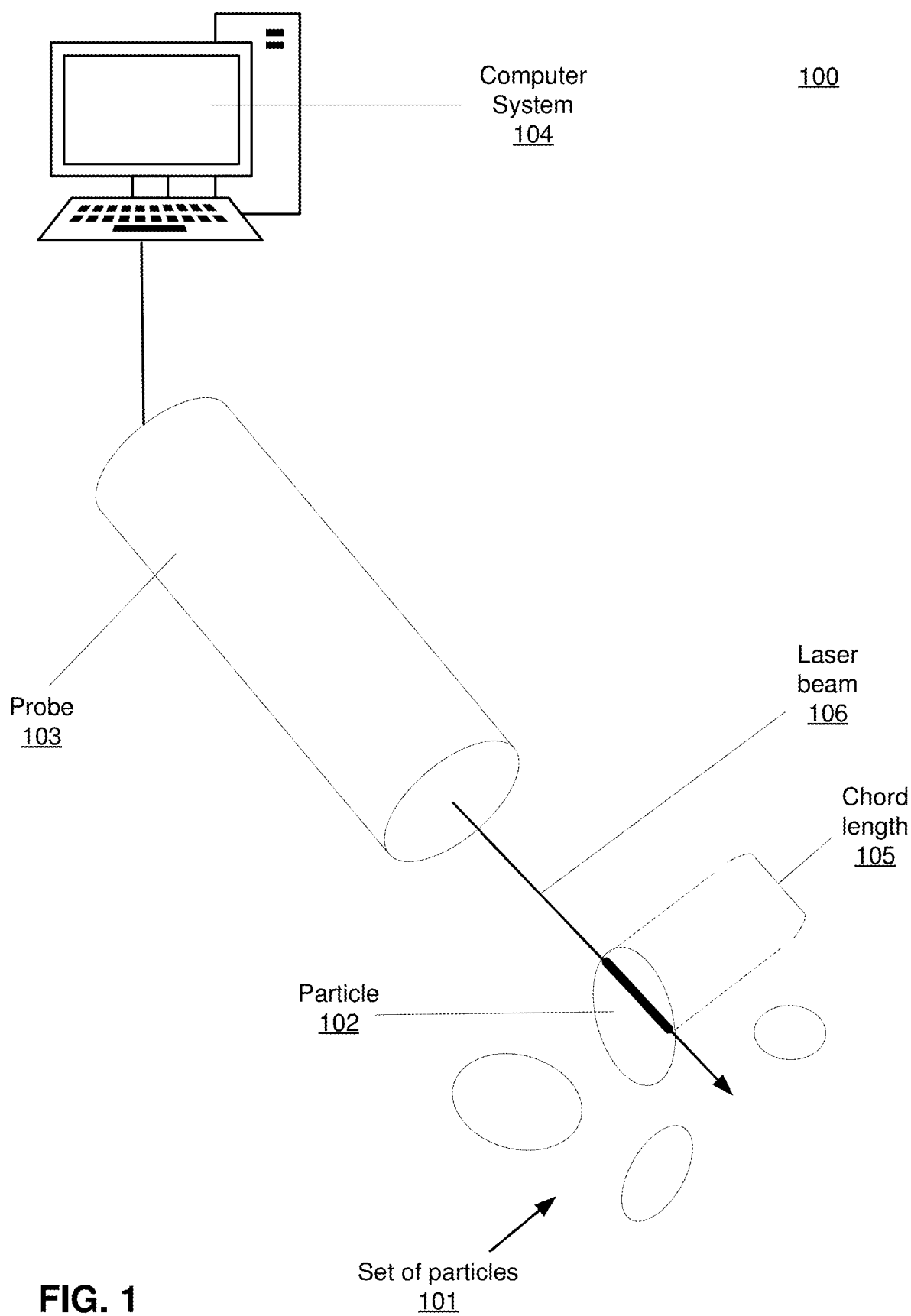
FIG. 1 is an illustration of a system for estimating a particle size distribution (PSD) and a morphology for a set of particles, in accordance with an embodiment.

FIG. 1 is an illustration of a system 100 for estimating a particle size distribution (PSD) and a morphology for a set of particles 101, in accordance with an embodiment. As shown in FIG. 1, the set of particles 101 includes four particles, including a particle 102. However, in alternative embodiments, the set of particles 101 may include any quantity of particles. As further shown in FIG. 1, the set of particles 101 includes particles of differing sizes, but a single morphology (e.g., an elongated morphology). However, in alternative embodiments, the set of particles 101 may include particles of the same size and/or differing morphologies.

As shown in FIG. 1, the system 100 includes a probe 103 and a computer system 104. The probe 103 is in communication with the computer system 104. In some embodiments, the probe 103 may be in communication with the computer system 104 via a hardware connection such as an electrical cable. In alternative embodiments, the probe 103 may be in wireless communication with the computer system 104. One embodiment of the architecture of the computer system 104 is discussed in further detail below with regard to FIG. 20.

The probe 103 is configured to determine chord length distribution (CLD) data of different types for the set of particles 101. This CLD data is used to generate CLDs of different types for the set of particles 101, as discussed in further detail below. CLD data for a set of particles includes chord length measurements for one or more particles in the set of particles. Therefore, CLD data for the set of particles 101 includes chord length measurements for one or more particles in the set of particles 101. For example, as shown in FIG. 1, CLD data for the set of particles 101 includes a chord length 105 for the particle 102. A chord of a particle is straight line segment whose endpoints both lie on an exterior surface of the particle. Therefore, a chord length of a particle is the length of a straight line segment whose endpoints both lie an exterior surface of the particle. In some embodiments, such as the embodiment depicted in FIG. 1, the probe 103 measures chord length for a particle, such as the particle 102, by emitting a laser beam 106 through the particle.

Following measurement of the CLD data of different types for the set of particles 101, including the chord length 105 of the particle 102, the probe 103 sends the CLD data to the computer system 104. The computer system 104 then determines a plurality of different types of CLDs for the set of particles 101 based on the CLD data received from the probe 103. Then, as discussed in further detail below with regard to FIGS. 4-19, the computer system 104 estimates a PSD and a morphology for the set of particles 101 based on the determined CLDs of different types.

In one embodiment, there are four types of CLD data (for clarity referred to herein as CLD type A, CLD type B, CLD type C, and CLD type D). Furthermore, each type of CLD data translates to a CLD of that type. For example, CLD data of type A is used to generate a CLD of type A. Similarly, CLD data of type D is used to generate a CLD of type D. An exemplar CLD is shown and discussed in further detail below with regard to FIG. 2.

Figure 2:
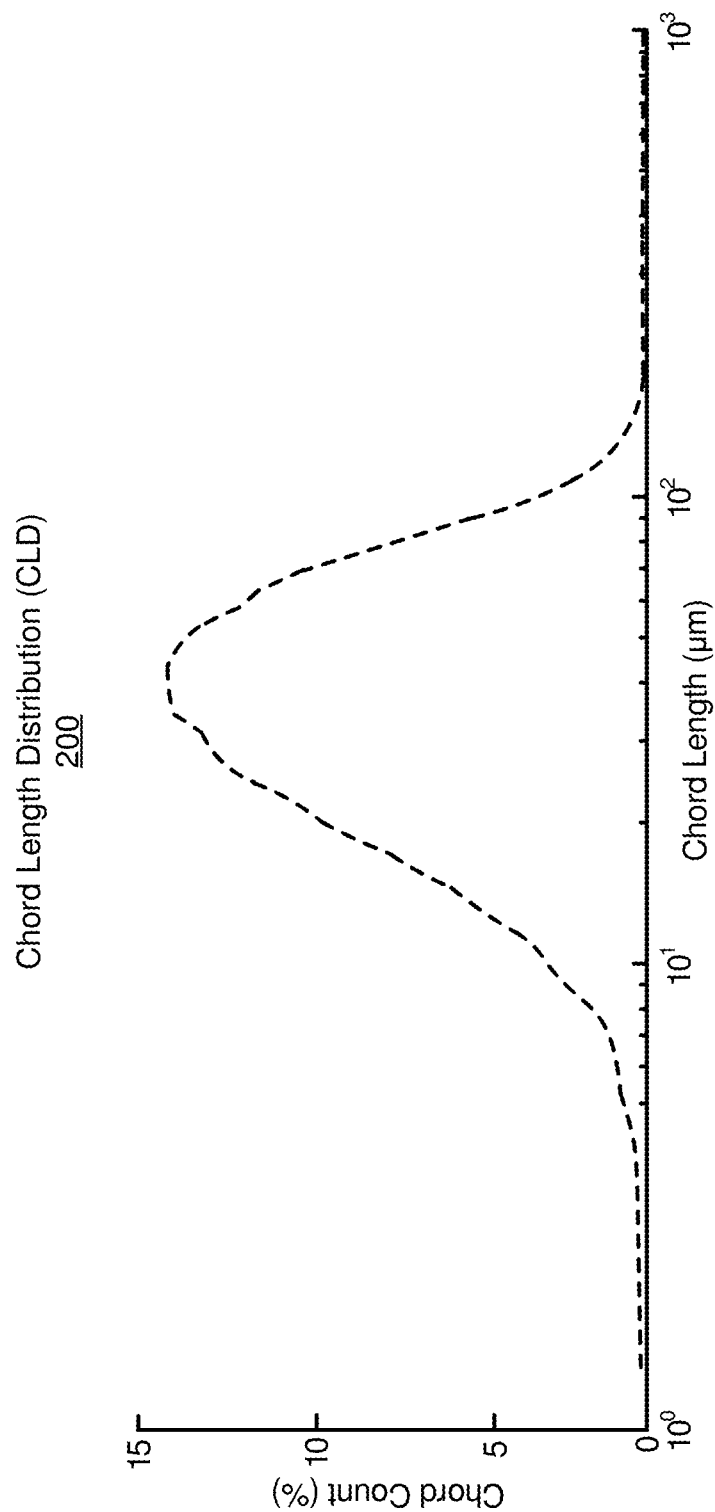
FIG. 2 is an illustration of an exemplar chord length distribution (CLD), in accordance with an embodiment.

FIG. 2 is an illustration of an exemplar CLD 200, in accordance with an embodiment. The exemplar CLD 200 depicts a portion of total chord count, by percentage, of particles in a set of particles that include each chord length over a range of chord lengths.

For each particle, a nearly infinite number of different chord lengths may be identified. Specifically, in embodiments in which chord length of a particle is measured by a probe, a nearly infinite number of different chord lengths may be identified for the particle depending upon the orientation of the probe and of the particle. This variability in chord length for a particle is further compounded for a set of particles, which results in a high level of variability in CLD data for the set of particles. As a result of this variability in CLD data for a set of particles, and for additional reasons discussed in further detail below with regard to FIGS. 3A-C, a CLD is an imprecise measure of particle size for a set of particles.

Figure 3A:
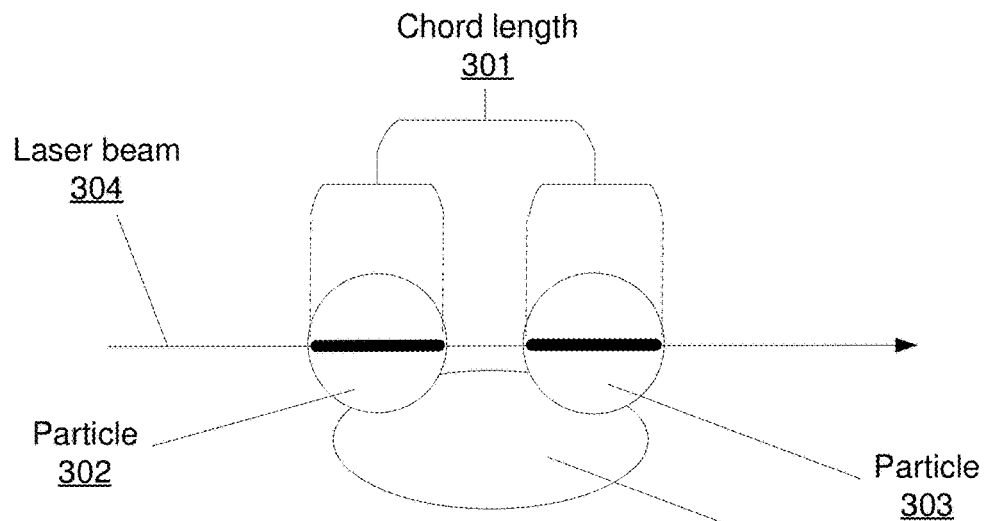
FIG. 3A illustrates a first example in which a chord length for a particle is measured inaccurately.
Figure 3B:
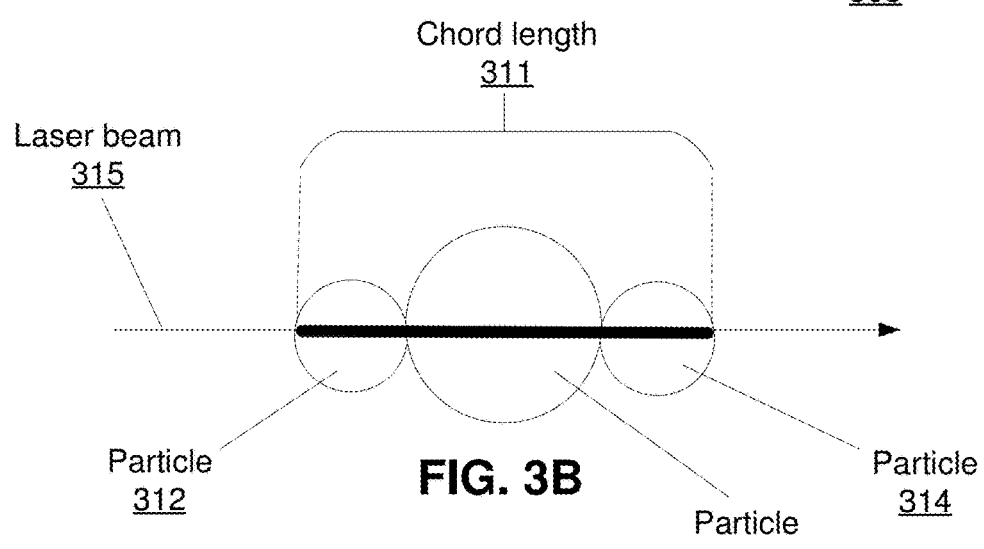
FIG. 3B illustrates a second example in which a chord length for a particle is measured inaccurately.
Figure 3C:
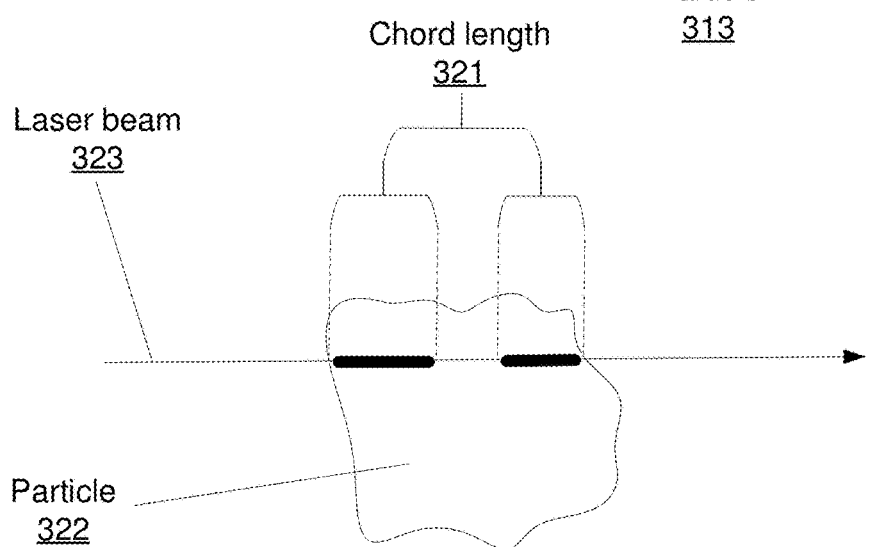
FIG. 3C illustrates a third example in which a chord length for a particle is measured inaccurately.

In addition to CLD being an imprecise measure of particle size, as demonstrated in FIGS. 3A-C, CLD can also be an inaccurate measure of particle size. Specifically, FIGS. 3A-C depict embodiments in which a chord length for a particle is measured inaccurately.

FIG. 3A illustrates a first example in which a chord length 301 for a particle 305 is measured inaccurately. As shown in FIG. 3A, three distinct particles, the particle 305, a particle 302, and a particle 303, are located near one another. To measure the chord length 301 of the particle 305, a laser beam 304 passes through the particles 302 and 303. However, the laser beam 304 does not measure the particle 305, because the particles 302 and 303 block this measurement. As a result, the chord length 301 identified for the particle 305 includes a sum of the chord lengths of the particle 302 and the particle 303. Therefore, the chord length 301 identified for the particle 305 is inaccurate.

FIG. 3B illustrates a second example in which a chord length 311 for a particle 312 is measured inaccurately. As shown in FIG. 3B, three distinct particles, the particle 312, a particle 313, and a particle 314, are positioned such that the particle 312 contacts the particle 313 and the particle 313 contacts the particle 314. To measure the chord length 311 of the particle 312, a laser beam 315 passes through the particle 312. However, the laser beam 315 continues on and also passes through the particle 313 and the particle 314. As a result, the chord length 311 identified for the particle 312 includes a sum of the chord lengths of the particle 312, the particle 313, and the particle 314. Therefore, the chord length 311 identified for the particle 312 is inaccurate.

FIG. 3C illustrates a third example in which a chord length 321 for a particle 322 is measured inaccurately. As shown in FIG. 3C, the particle 322 has irregular edges. To measure the chord length 321 of the particle 322, a laser beam 323 passes through the particle 322. However, as a result of the irregular edges of the particle 322, the chord length 321 identified for the particle 322 does not include the entire chord length of the particle 322. Rather the identified chord length 321 includes just two segments of the actual chord length of the particle 322. Therefore, the chord length 321 identified for the particle 322 is inaccurate.

As discussed above with regards to FIGS. 2 and 3A-C, a CLD is both an imprecise and an inaccurate measure of particle size for a set of particles. Therefore, an alternative and more reliable measurement of particle size, such as PSD, is desirable. Accordingly, methods for determining PSD for a set of particles are discussed in further detail below with regard to FIGS. 4-18.

CLD Type Specific, Morphology Specific System Architecture

Figure 4:
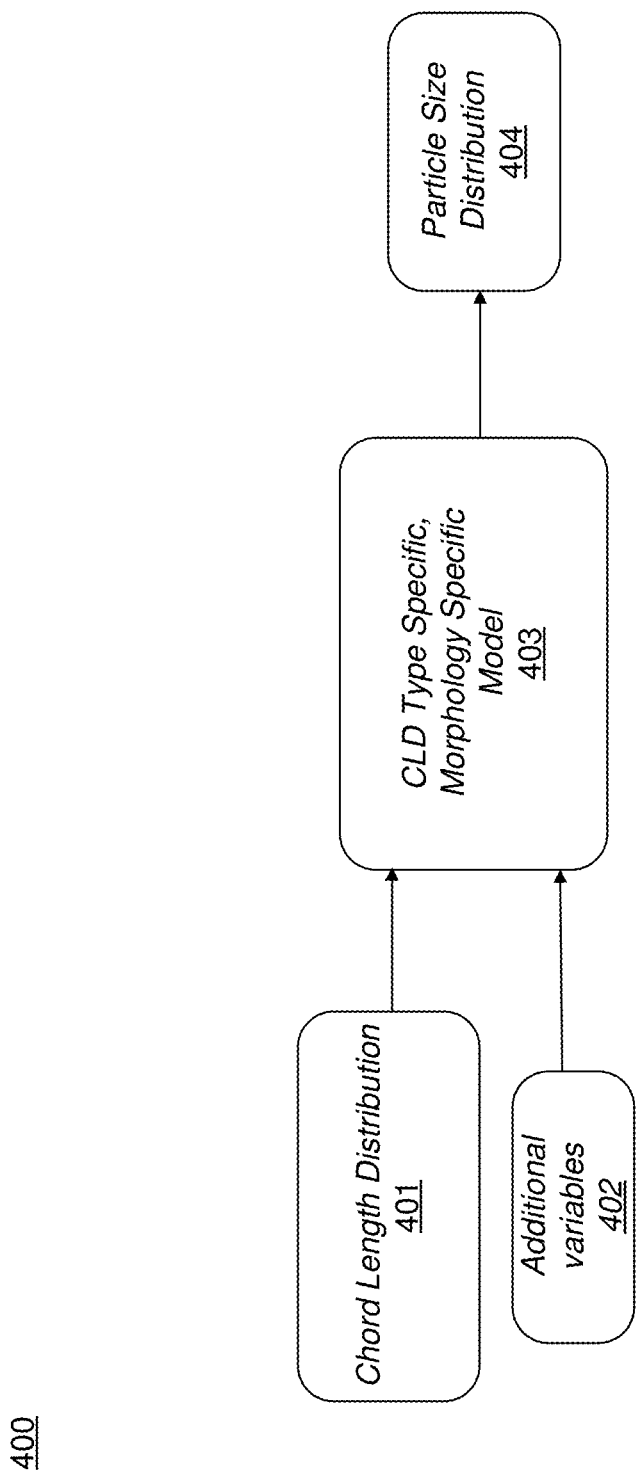
FIG. 4 is a system diagram of a system for generating a PSD for a set of particles, in accordance with an embodiment.

FIG. 4 is a system diagram 400 of a system for generating a PSD 404 for a set of particles, in accordance with an embodiment. In the embodiment shown in FIG. 4, to generate a PSD 404 for a set of particles, a CLD 401 for the set of particles, and in some embodiments additional variables 402 for the set of particles, are input into a model 403. The model 403 subsequently determines and outputs the PSD 404 based on the CLD 401 and in some embodiments, the additional variables 402. An exemplar PSD is discussed in further detail below with regard to FIG. 6.

As discussed above with regard to FIG. 1, the CLD 401 for a set of particles can be determined using a probe in communication with a computer system. Specifically, the probe determines CLD data for the set of particles, and sends the determined CLD data to the computer system. The computer system then generates the CLD 401 for the set of particles based on the received CLD data. The CLD 401 is then input into the model 403 as described above. The additional variables 402 that can be input into the model 403 in addition to the CLD 401 include, for example, a slurry concentration for the set of particles.

Prior to describing the architecture of the model 403, it should be noted that the embodiment of the model 403 shown operates in three distinct phases: a training phase, a validation phase, and a testing phase. During the training phase, the model 403 is trained to accurately generate a PSD 404 based on a CLD 401, and in some embodiments, additional variables 402 input into the model 403. The model 403 is trained using a training dataset. The training dataset includes a plurality of training samples. Each training sample is associated with a training set of particles, and includes input(s) and a verified output. To train the model 403 using the training dataset, the input(s) of each training sample from the training dataset are input into the model 403. The model 403 subsequently generates an output based on those input(s). The output generated by the model 403 is compared with the verified output of the training sample. Based on this comparison between the output generated by the model 403 and the verified output of the training sample, the parameters of the model 403 are modified to enable the model 403 to generate more accurate outputs in future uses. Training of the model 403 is discussed in further detail below with regard to FIG. 5.

During the validation phase, the model 403 is validated to determine whether the model 403 has been sufficiently trained to accurately generate a PSD 404 based on a CLD 401, and in some embodiments additional variables 402, input into the model 403. The model 403 is validated using a validation dataset. The validation dataset includes a plurality of validation samples. Similar to the training samples, each validation sample is associated with a validation set of particles and includes input(s) and a verified output. However, to ensure reliable validation of the model 403, the validation dataset includes different samples than the training data set. To validate the model 403 using the validation dataset, the input(s) of each validation sample from the validation dataset are input into the model 403. The model 403 subsequently generates an output based on those input (s). Then, the output generated by the model 403 is compared with the verified output of the validation sample. Based on this comparison between the output generated by the model 403 and the verified output of the validation sample, the model 403 re-enters the training phase, or moves on to the testing phase. Specifically, if a discrepancy between the output generated by the model 403 and the verified output of the validation sample is equal to or less than threshold discrepancy, the model 403 is considered validated, and the model moves on to the testing phase. However, if a discrepancy between the output generated by the model 403 and the verified output of the validation sample is greater than the threshold discrepancy, the model 403 is not considered to be validated, and re-enters the training phase to undergo further training. Validation of the model 403 is discussed in further detail below with regard to FIG. 5.

Following both training and validation of the model 403, the model 403 enters the testing phase. During the testing phase, the model receives inputs of a CLD 401, and in some embodiments additional variables 402, and generates an output of a PSD 404. The accuracy of the PSD 404 output by the model 403 during the testing phase depends on the quality and quantity of training and validation during the training and validation phases, respectively. Specifically, the higher the quantity and quality of training and validation of the model 403, the more accurate the PSD 404 output by the model 403 during testing.

Turning to a discussion of the architecture of the model 403, as seen in FIG. 4, the model 403 that generates the PSD 404 for a set of particles is CLD type specific and particle morphology specific. In other words, the model 403 is configured to generate PSDs 404 for sets of particles including particles of a single, specific particle morphology, based on a single, specific type of CLD 401. Specifically, the model 403 is configured to generate PSDs 404 for sets of particles including particles of a specific particle morphology and for types of CLDs 401 on which the model 403 was previously trained and validated. For example, to generate a PSD 404 for a set of particles including particles with an elongated particle morphology, based on a CLD 401 of type B using the model 403, the model 403 is trained and validated only on CLDs 401 of type B for sets of particles including particles with the elongated particle morphology.

Due to the specificity of the model 403 to a particular particle morphology and a particular CLD type, various embodiments train and validate a different model 403 for each different combination of particle morphology and CLD type. For example, to predict a PSD for a set of particles including particles with a circular morphology based on a CLD 401 of type C, a first model 403 is trained and validated using a training dataset and a validation dataset including particles of the circular morphology and CLDs of type C. Then, to predict a PSD for a set of particles including particles with an elongated morphology based on a CLD 401 of type C, a second model 403, distinct from the first model 403, is trained and validated using a training and validation dataset including particles of the elongated morphology and CLDs of type C. Therefore, the specificity of the model 403 to a particular type of CLD and to a particular particle morphology results in a need for a plurality of distinct models 403, each trained and validated based on a training dataset and a validation dataset including a different combination of particle morphology and CLD type.

As discussed with regard to FIG. 1, in one embodiment, there are four types of CLDs. Additionally, there are a range of different particle morphologies. As such, a large quantity of training and validation samples may be required to train and validate a different model 403 for each combination of particle morphology and CLD type. And furthermore, each training, validation, and testing sample should include primarily particles including the single morphology associated with the model 403 operating on the sample. It can be difficult to identify the morphology of particles in a sample, and therefore it can be difficult to identify samples that can be used by a model 403 associated with a particular particle morphology. Additionally, the morphology of particles in a sample may be unstable, as discussed in further detail below with regard to FIGS. 7A-E. Finally, training, validating, and storing a different model 403 for each combination of particle morphology and CLD type places a strain on the computer system. Accordingly, in some embodiments it may be desirable to have a different model that is not specific to a CLD type and a particle morphology. In other words, it may be desirable to have a model that is non-specific to CLD type and to particle morphology. Such embodiments are discussed in further detail below with regard to FIG. 8.

Figure 5:
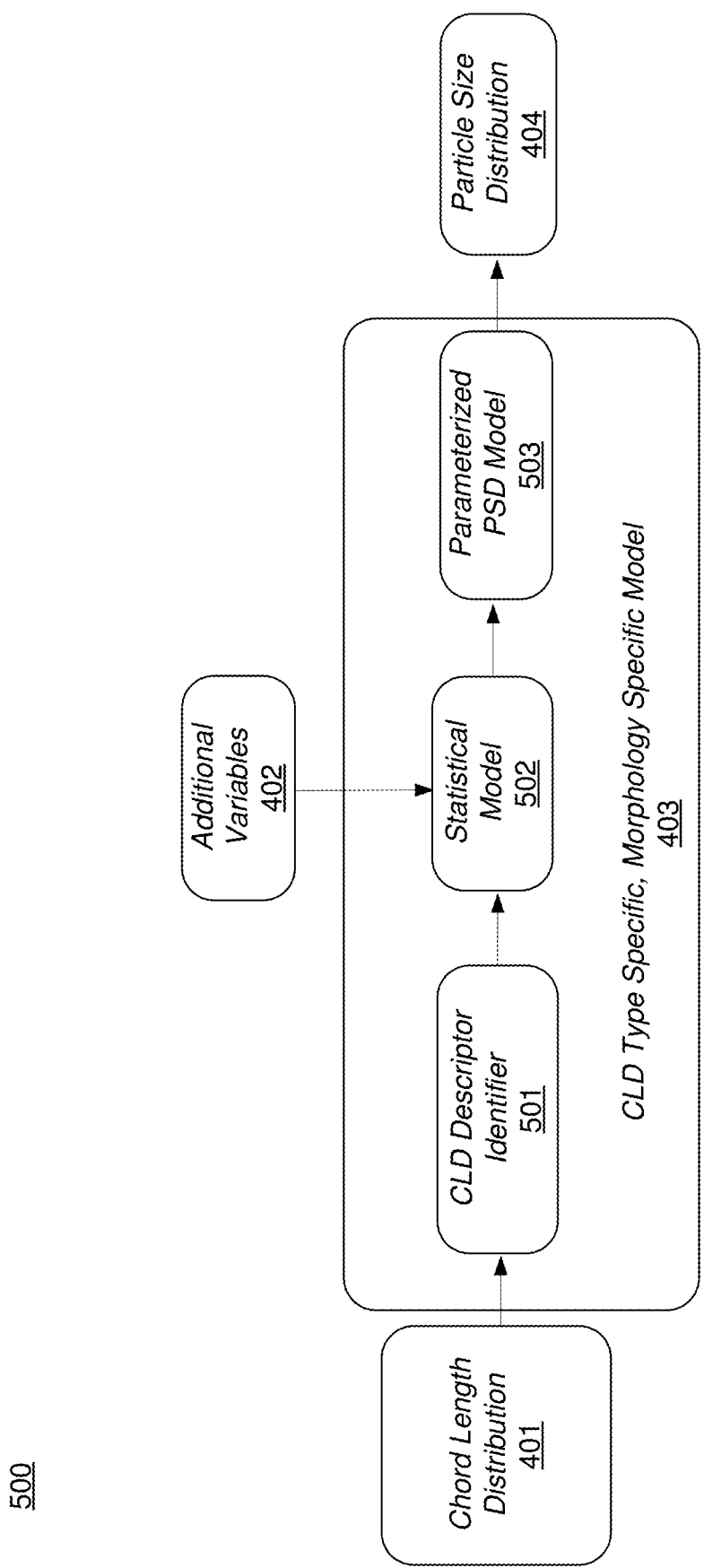
FIG. 5 is a system diagram of the CLD type specific, morphology specific model of FIG. 4, in accordance with an embodiment.

FIG. 5 is a system diagram 500 of the CLD type specific, morphology specific model 403 of FIG. 4, in accordance with an embodiment. As discussed above with regard to FIG. 4, a CLD 401, and in some embodiments additional variables 402, are input into the model 403, and the model 403 subsequently outputs a PSD 404. As also discussed above with regard to FIG. 4, the model 403 is both CLD type and morphology specific. In other words, the model 403 generates a PSD 404 for a set of particles including particles of a specific morphology, and for a CLD 401 of a specific type, on which the model 403 was trained and validated.

In the embodiment of the model 403 depicted in FIG. 5, the model 403 includes three separate, sequential components. Specifically, the model 403 includes a CLD descriptor identifier 501, a statistical model 502, and a parameterized PSD model 503.

Turning first to the CLD descriptor identifier 501, the CLD descriptor identifier 501 receives the CLD 401 and outputs a plurality of descriptors of the CLD 401. In some embodiments, the plurality of descriptors of the CLD 401 that are output by the CLD descriptor identifier include one or more moments of the CLD 401.

Turning next to the statistical model 502, the statistical model 502 receives the plurality of descriptors of the CLD 401 output by the CLD descriptor identifier 501. In some embodiments, the statistical model 502 also receives the additional variables 402 discussed above with regard to FIG. 4. As noted above, the additional variables 402 can include, for example, a slurry concentration for the set of particles associated with the CLD 401. The statistical model 502 then estimates metrics for the PSD 404 based on the plurality of identified descriptors, and in some embodiments, the additional variables 402. In certain embodiments, the statistical model includes a regression model that is configured to perform regression analysis to estimate the metrics for the PSD 404.

Turning finally to the parameterized PSD model 503, the parameterized PSD model 503 receives the PSD metrics output by the statistical model 502, and generates an estimate of the PSD 404 based on the PSD metrics. This estimate of the PSD 404 is subsequently output by the model 403. In some embodiments, the parameterized PSD model 503 includes a neural network model.

As discussed above with regard to FIG. 4, prior to using the model 403 for testing, the model 403 is trained and validated. In some embodiments, the model 403 is trained and validated as a single unit. In such embodiments, each training sample in the plurality of training samples that includes the training dataset includes a CLD 401 as an input and a PSD 404 as a verified output. As discussed above, each training sample in the training dataset is based on particles including a single morphology, and on a single type of CLD data. The CLD 401 is input into the model 403, and the model 403 subsequently outputs a PSD 404 based on the CLD 401. Then, the PSD 404 output by the model 403 is compared with the verified PSD 404 of the training sample. Based on this comparison between the PSD 404 output by the model 403 and the verified PSD 404 of the training sample, the parameters of the model 403 are modified to enable the model 403 to generate more accurate PSDs 404 in future uses. Similarly, in such embodiments in which the model 403 is validated as a single unit, each validation sample in the plurality of validation samples that includes the validation dataset includes a CLD 401 as an input and a PSD 404 as a verified output. Each validation sample in the validation dataset is based on particles including a single morphology, and on a single type of CLD data. The CLD 401 is input into the model 403, and the model 403 subsequently outputs a PSD 404 based on the CLD 401. Then, the PSD 404 output by the model is compared with the verified PSD 404 of the validation sample. Based on this comparison between the PSD 404 output by the model 403 and the verified PSD 404 of the validation sample, either the model 403 is considered validated, and the model moves on to the testing phase, or the model 403 is not considered to be validated, and re-enters the training phase to undergo further training.

In alternative embodiments, the model 403 is not trained and validated as a single unit, but rather, each individual component of the model 403 is separately trained and separately validated. Specifically, in alternative embodiments, each of the CLD descriptor identifier 501, the statistical model 502, and the parameterized PSD model 503 are separately trained and validated using corresponding training and validation datasets, respectively. Specifically, in such embodiments, the CLD descriptor identifier 501 is trained and validated using a first training and validation dataset, respectively, the statistical model 502 is trained and validated using a second training and validation dataset, respectively, and the parameterized PSD model 503 is trained and validated using a third training and validation dataset, respectively. As discussed above, for a given model 403, each training sample in the training dataset for each of the three components of the model 403, and each validation sample in the validation dataset for each of the three components of the model 403, is based on particles including a single particle morphology, and on a single type of CLD data.

Each training sample in the plurality of training samples that includes the training dataset for the CLD descriptor identifier 501 includes a CLD 401 as an input and a plurality of descriptors of the CLD 401 as a verified output. The CLD 401 is input into the CLD descriptor identifier 501, and the CLD descriptor identifier 501 subsequently outputs a plurality of descriptors based on the CLD 401. Then, the plurality of descriptors output by the CLD descriptor identifier 501 is compared with the verified plurality of descriptors of the training sample. Based on this comparison between the plurality of descriptors output by the CLD descriptor identifier 501 and the verified plurality of descriptors of the training sample, the parameters of the CLD descriptor identifier 501 are modified to enable the CLD descriptor identifier 501 to generate more accurate descriptors in future uses. Similarly, in such embodiments in which the CLD descriptor identifier 501 is validated as a single unit, each validation sample in the plurality of validation samples that includes the validation dataset includes a CLD 401 as an input and a plurality of descriptors as a verified output. The CLD 401 is input into the CLD descriptor identifier 501, and the CLD descriptor identifier 501 subsequently outputs a plurality of descriptors based on the CLD 401. Then, the plurality of descriptors output by the model is compared with the verified plurality of descriptors of the validation sample. Based on this comparison between the plurality of descriptors output by the CLD descriptor identifier 501 and the verified plurality of descriptors of the validation sample, either the CLD descriptor identifier 501 is considered validated, and the model moves on to the testing phase, or the CLD descriptor identifier 501 is not considered to be validated, and re-enters the training phase to undergo further training.

Similarly, each training sample in the plurality of training samples that includes the training dataset for the statistical model 502 includes a plurality of descriptors for the CLD 401 as an input and PSD metrics for the PSD 404 as a verified output. In some embodiments, each training sample in the training dataset also includes a slurry concentration as an input. The plurality of descriptors, and in some embodiments the slurry concentration, are input into the statistical model 502, and the statistical model 502 subsequently outputs PSD metrics based on the plurality of descriptors, and in some embodiments the slurry concentration. Then, the PSD metrics output by the statistical model 502 are compared with the verified PSD metrics of the training sample. Based on this comparison between the PSD metrics output by the statistical model 502 and the verified PSD metrics of the training sample, the parameters of the statistical model 502 are modified to enable the statistical model 502 to generate more accurate PSD metrics in future uses. Similarly, in such embodiments in which the statistical model 502 is validated as a single unit, each validation sample in the plurality of validation samples that includes the validation dataset includes a plurality of descriptors for the CLD 401 as an input and PSD metrics for the PSD 404 as a verified output. In some embodiments, each validation sample in the validation dataset also includes a slurry concentration as an input. The plurality of descriptors, and in some embodiments the slurry concentration, are input into the statistical model 502, and the statistical model 502 subsequently outputs PSD metrics based on the plurality of descriptors, and in some embodiments the slurry concentration. Then, the PSD metrics output by the model are compared with the verified PSD metrics of the validation sample. Based on this comparison between the PSD metrics output by the statistical model 502 and the verified PSD metrics of the validation sample, either the statistical model 502 is considered validated, and the model moves on to the testing phase, or the statistical model 502 is not considered to be validated, and re-enters the training phase to undergo further training.

Similarly, for the parameterized PSD model 503, each training sample in the plurality of training samples that includes the training dataset for the parameterized PSD model 503 includes PSD metrics for the PSD 404 as an input and a PSD 404 as a verified output. The PSD metrics are input into the parameterized PSD model 503, and the parameterized PSD model 503 subsequently outputs a PSD 404 based on the PSD metrics. Then, the PSD 404 output by the parameterized PSD model 503 is compared with the verified PSD 404 of the training sample. Based on this comparison between the PSD 404 output by the parameterized PSD model 503 and the verified PSD 404 of the training sample, the parameters of the parameterized PSD model 503 are modified to enable the parameterized PSD model 503 to generate a more accurate PSD 404 in future uses. Similarly, in such embodiments in which the parameterized PSD model 503 is validated as a single unit, each validation sample in the plurality of validation samples that includes the validation dataset includes PSD metrics for the PSD 404 as an input and a PSD 404 as a verified output. The PSD metrics are input into the parameterized PSD model 503, and the parameterized PSD model 503 subsequently outputs a PSD 404 based on the PSD metrics. Then, the PSD 404 output by the model is compared with the verified PSD 404 of the validation sample. Based on this comparison between the PSD 404 output by the parameterized PSD model 503 and the verified PSD 404 of the validation sample, either the parameterized PSD model 503 is considered validated, and the model moves on to the testing phase, or the parameterized PSD model 503 is not considered to be validated, and re-enters the training phase to undergo further training.

Figure 21:
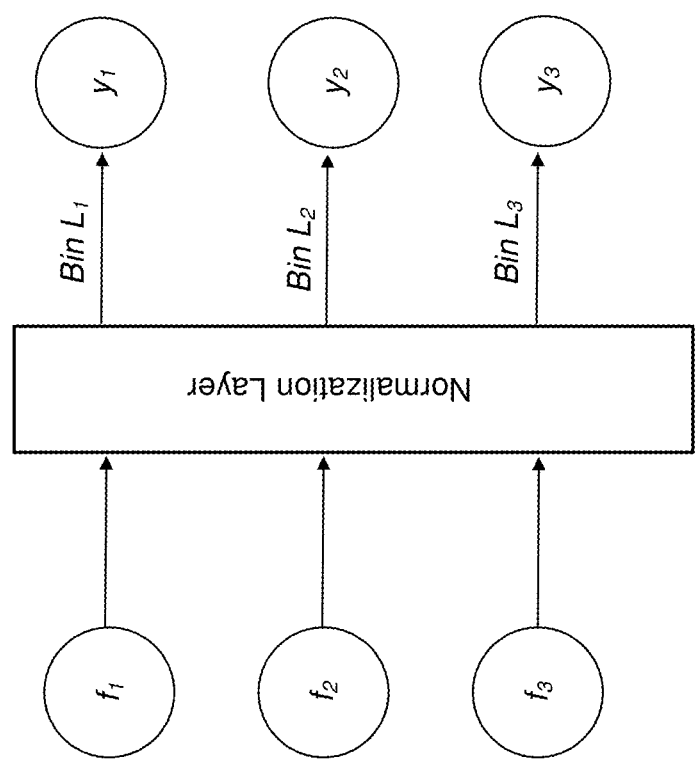
FIG. 21 depicts a parameterized PSD model that includes a neural network model, in accordance with an embodiment.

In embodiments in which the descriptor identifier 501 is trained and validated as a single unit, in general the descriptor includes a function representing a relation between a chord length distribution for a set of particles identifier 501 and a plurality of identified descriptors of the chord length distribution for the set of particles, the function based on a training dataset for the descriptor identifier 501. In embodiments in which the statistical model 502 is trained and validated as a single unit, in general the statistical model 502 includes a function representing a relation between a plurality of identified descriptors for a CLD 401 and PSD metrics for a PSD 404, the function based on a training dataset for the statistical model 402. Similarly, in embodiments in which the parameterized PSD model 503 is trained and validated as a single unit, in general the parameterized PSD model 503 includes a function representing a relation between PSD metrics for a PSD 404 and the PSD 404, the function based on a training dataset for the parameterized PSD model 503. FIG. 21 depicts a parameterized PSD model 503 that includes a neural network model 2100, in accordance with an embodiment. The embodiment of the neural network model 2100 depicted in FIG. 21 includes a two layer neural network model. In alternative embodiments, the neural network model 2100 may include any number of layers.

The first layer of the neural network model 2100 is an input layer including three nodes. In alternative embodiments, the first layer of the neural network model 2100 may include any number of nodes. Each node in the first layer of the neural network 2100 includes a generating function that is configured to receive a PSD metric as an input from the statistical model 502 of FIG. 5. One embodiment of a generating function is depicted and is discussed in further detail below with regard to FIG. 22. The output of each generating function in the first layer of the neural network 2100 is an input of the second layer of the neural network model 2100.

The second layer of the neural network model 2100 is a normalization layer. The second layer of the neural network model 2100 receives outputs from the generating functions in the first layer of the neural network 2100, and outputs a value $y_i$ to each node of the output layer of the neural network model 2100. Therefore, the number of values $y_i$ output by the second layer of the neural network model 2100 corresponds to the number of nodes in the output layer of the neural network model 2100. As discussed below, in the embodiment of the neural network model 2100 depicted in FIG. 21, the output layer of the neural network model 2100 includes three nodes. Therefore, the second layer of the neural network model 2100 outputs three values $y_i$, each value $y_i$ associated with a node of the output layer of the neural network model 2100. The significance of the nodes of the output layer of the neural network, and of the values $y_i$, is discussed in further detail below.

Each node (e.g., each generating function) in the input layer (e.g., the first layer) of the neural network model 2100 corresponds to a node in the output layer of the neural network model 2100. Therefore, the number of nodes in the output of the neural network model 2100 equals the number of nodes in the input layer of the neural network model 2100. As noted above, in the embodiment of the neural network model 2100 depicted in FIG. 21, the input layer of the neural network model 2100 includes three nodes. Therefore, the output layer of the neural network model 2100 also includes three nodes.

Each node in the output layer of the neural network model 2100 is associated with a bin coordinate $L_i$. Each bin coordinate $L_i$ corresponds to a range of particle sizes. For example, a bin coordinate $L_2$ may correspond to particles of sizes between 1 and 10 µm. Each value $y_i$ output by the second layer of the neural network model 2100 corresponds to an absolute or relative quantity of particles of a given size. For example, a value $y_2$ may correspond to 1% of a total volume of particles.

As noted above, each value $y_i$ output by the second layer of the neural network model 2100 is associated with a node of the output layer of the neural network model 2100. Because each node of the output layer of the neural network model 2100 is associated with a bin coordinate $L_i$, each value $y_i$ is associated a bin coordinate $L_i$. For example, as shown in FIG. 21, the value $y_2$ is associated with the bin coordinate $L_2$. Thus, for the example given above, 1% of a total volume of particles includes particles of sizes between 1 and 10 µm. Using each value $y_i$ to bin coordinate $L_i$ association depicted in the output layer of the neural network model 2100, a PSD can be generated for a set of particles associated with the PSD metrics input into the neural network model 2100. The generated PSD depicts portion of total volume, by percentage, of particles in a set of particles that include each particle size over a range of particles sizes. An example PSD is depicted and discussed in detail below with regard to FIG. 7.

Figure 22:
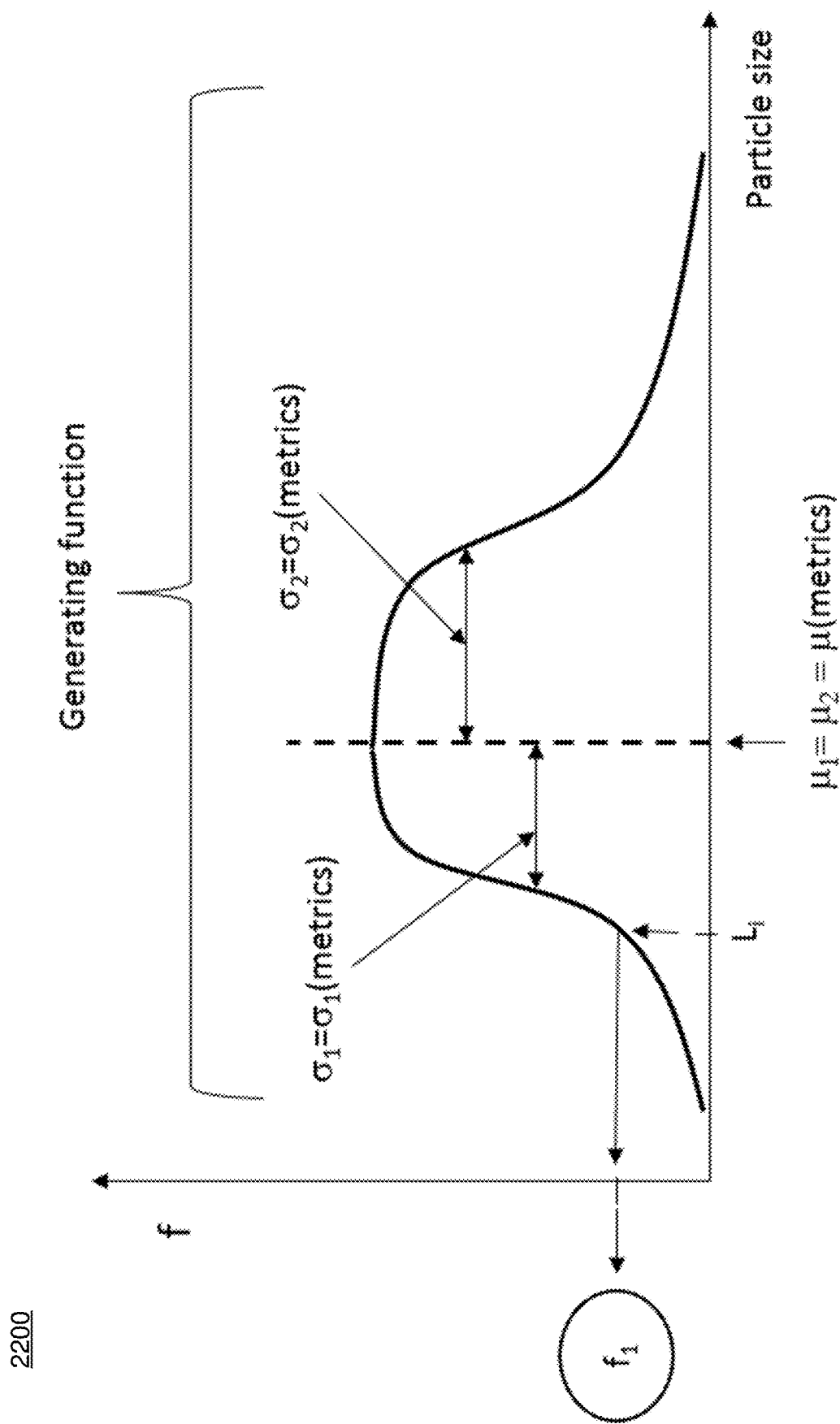
FIG. 22 depicts a generating function, in accordance with an embodiment.

FIG. 22 depicts a generating function 2200, in accordance with an embodiment. The generating function 2200 is a surrogate function that enables calculation of the neural network model node values ($f_i$) in FIG. 21 with a small number of parameters.

The generating function 2200 consists of patches of simple functions (e.g., Gaussians functions) in which parameters are not fixed, but are functions of the metrics determined by the statistical model 502. FIG. 22 depicts a generating function 2200 consisting of patches of two Gaussian functions. A first Gaussian function is located on the left side of the mean (m(metrics)), and a second Gaussian function is located on the right side of the mean (m(metrics)). Both Gaussian functions share the same mean ($m_1 = m_2$), which is determined as a function of the metrics (m(metrics)) from the statistical model 502. Each Gaussian function has a different standard deviation ($s_1$ for the first Gaussian function and $s_2$ for the second Gaussian function). Each Gaussian function is not fixed but a function of the metrics ($s_1$(metrics) for the first Gaussian function and $s_2$(metrics) for the second Gaussian function).

In one embodiment, for values below the mean (m(metrics)), the generating function 2200 equals the value of the first Gaussian function, and for values larger than the mean, the generating function 2200 equals the value of the second Gaussian function. At each value of the mean (m(metrics)), the value of the generating function 2200 is assigned to the corresponding node value ($f_i$) in FIG. 21. The functions (m, s1, s2) have a small number of undefined parameters.

FIG. 22 is one example of a generating function 2200. Alternative embodiments of generating function may also be used in alternative embodiments.

Figure 6:
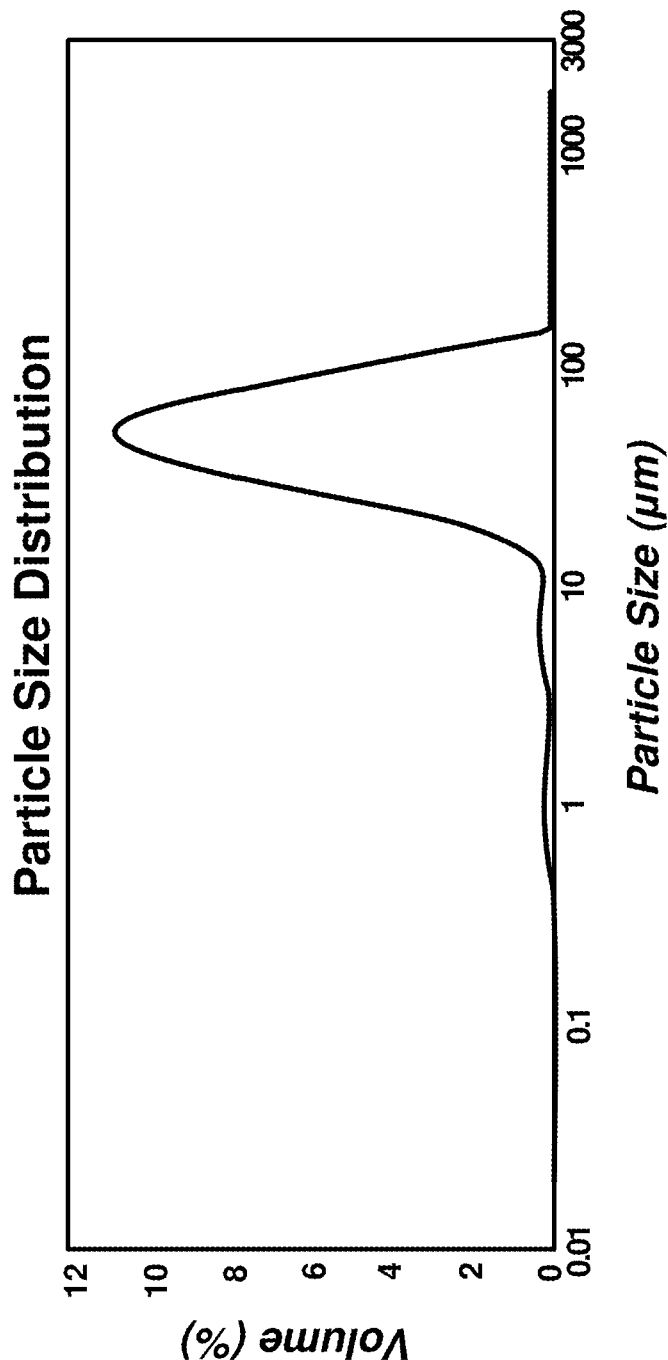
FIG. 6 depicts an exemplar PSD, in accordance with an embodiment.

FIG. 6 depicts an exemplar PSD 600, in accordance with an embodiment. As briefly mentioned above, the exemplar PSD 600 depicts the portion of total volume, by percentage, of particles in a set of particles that include each particle size over a range of particles sizes. Specifically, the exemplar PSD 600 depicts the portion of total volume, by percentage, of particles in a set of particles that include each particle size between 0 and 3000 µm.

System Architecture: Multiple CLD Types, Multiple Morphologies

As discussed above, the model 403 depicted in FIG. 4 that generates a PSD 404 for a set of particles is particle morphology specific, and also CLD type specific. Specifically, the model 403 is configured to generate a PSD 404 for a set of particles including particles of a single, specific particle morphology and for a type of CLD 401 on which the model 403 was previously trained and validated. Therefore a large quantity of training and validation samples may be required to train and validate a different model 403 for each combination of particle morphology and CLD type. And furthermore, training, validating, and storing a different model 403 for each combination of particle morphology and CLD type places a strain on the computer system performing these tasks.

In addition to the above constraints imposed by the model 403, due to the particle morphology specificity of the model 403, each training, validation, and testing sample used by the model 403 should be based primarily on particles including the single morphology associated with the model 403 operating on the sample. It can be difficult to identify the morphology of particles in a sample, and therefore it can be difficult to identify the samples that can be used by a model 403 associated with a particular particle morphology. Additionally, the morphology of particles in a sample may be unstable. Specifically, particles in a sample may change in morphology according to one or more dominant particle formation mechanisms, thereby transforming a sample with particles of a morphology A into a sample with particles of a morphology B, and thereby rendering the sample unfit for use by a model 403 associated with the morphology A.

Figure 7A:
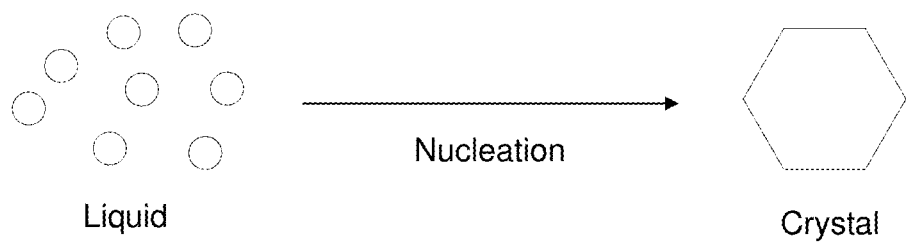
FIG. 7A depicts nucleation of a set of liquid particles into a crystalline particle, in accordance with an embodiment.
Figure 7B:
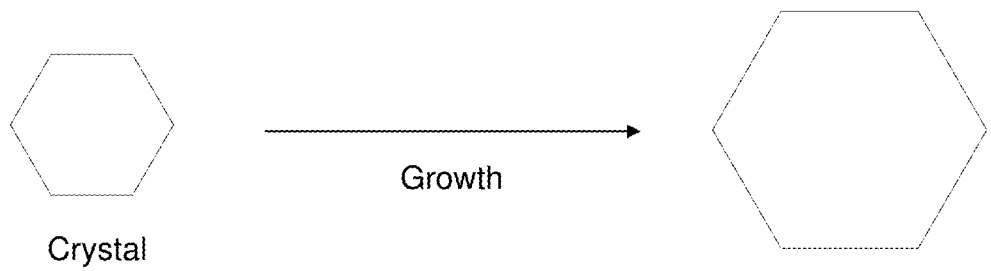
FIG. 7B depicts growth of a relatively smaller crystalline particle into a relatively larger crystalline particle, in accordance with an embodiment.
Figure 7C:
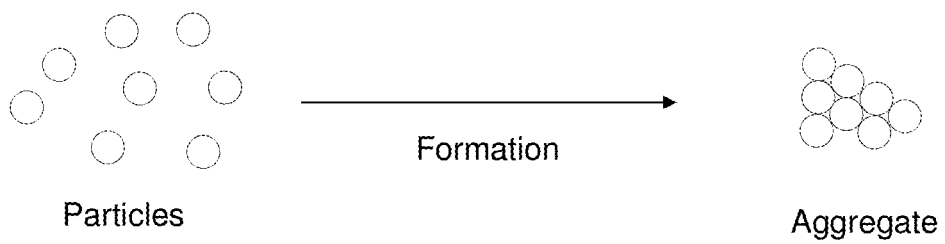
FIG. 7C depicts formation of a set of particles into an aggregate particle, in accordance with an embodiment.
Figure 7D:
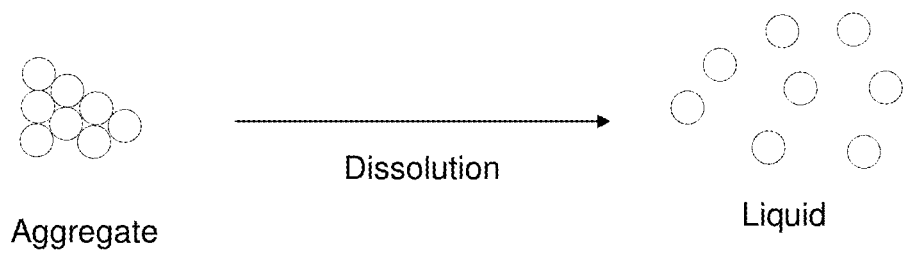
FIG. 7D depicts dissolution of an aggregate particle into a set of liquid particles, in accordance with an embodiment.
Figure 7E:
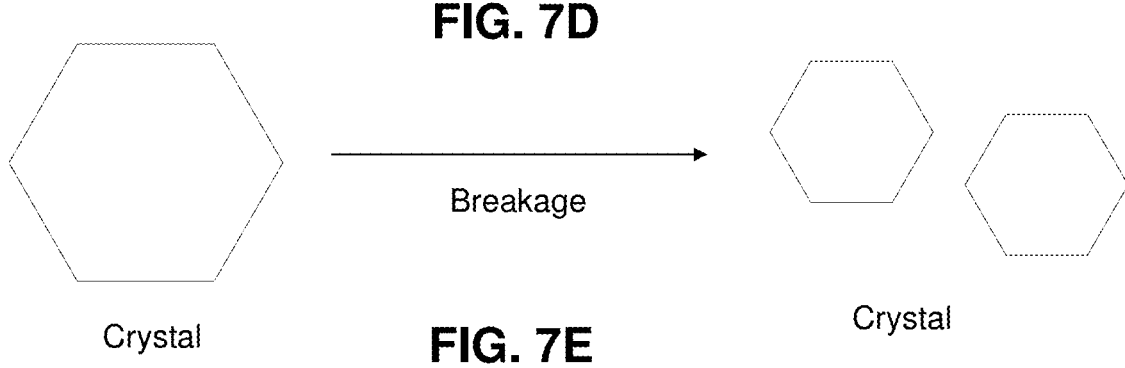
FIG. 7E depicts breakage of a crystalline particle into a set of crystalline particles, in accordance with an embodiment.

FIGS. 7A-E depict examples of dominant particle formation mechanisms that may result in a morphology change for one or more particles, in accordance with an embodiment. Specifically, FIG. 7A depicts nucleation of a set of liquid particles into a crystalline particle, in accordance with an embodiment. FIG. 7B depicts growth of a relatively smaller crystalline particle into a relatively larger crystalline particle, in accordance with an embodiment. FIG. 7C depicts formation of a set of particles into an aggregate particle, in accordance with an embodiment. FIG. 7D depicts dissolution of an aggregate particle into a set of liquid particles, in accordance with an embodiment. And finally, FIG. 7E depicts breakage of a crystalline particle into a set of crystalline particles, in accordance with an embodiment. FIGS. 7A-E depict a few examples of dominant particle formation mechanisms. Different or additional dominant particle formation mechanisms, in addition to the dominant particle formation mechanisms depicted in FIGS. 7A-E, may also be present in any given sample.

In some of the above examples of dominant particle formation mechanisms, one or more particles experiences a change in morphology. Specifically, morphology changes occur as a result of the dominant particle formation mechanisms depicted in FIGS. 7A, 8C, and 8D. In FIG. 7A, nucleation changes a set of liquid particles into a crystalline particle. In FIG. 7C, formation changes a set of particles into an aggregate particle. And in FIG. 7D, dissolution changes an aggregate particle into a set of liquid particles. As briefly discussed above, such changes in morphology of one or more particles in a sample can transform a sample with particles of a morphology A into a sample with particles of a morphology B, thereby rendering the sample unfit for use by a model 403 associated with the morphology A. Therefore, in some embodiments, it may be desirable to have access to a model that is not specific to particle morphology or CLD type. Furthermore, in addition to being able to generate a PSD for a set of particles including particles of any morphology, it may be further desirable for the model to possess the ability to estimate a morphology of the particles in a set of particles. A model with such capabilities is discussed in detail below with regard to FIG. 8.

Figure 8:
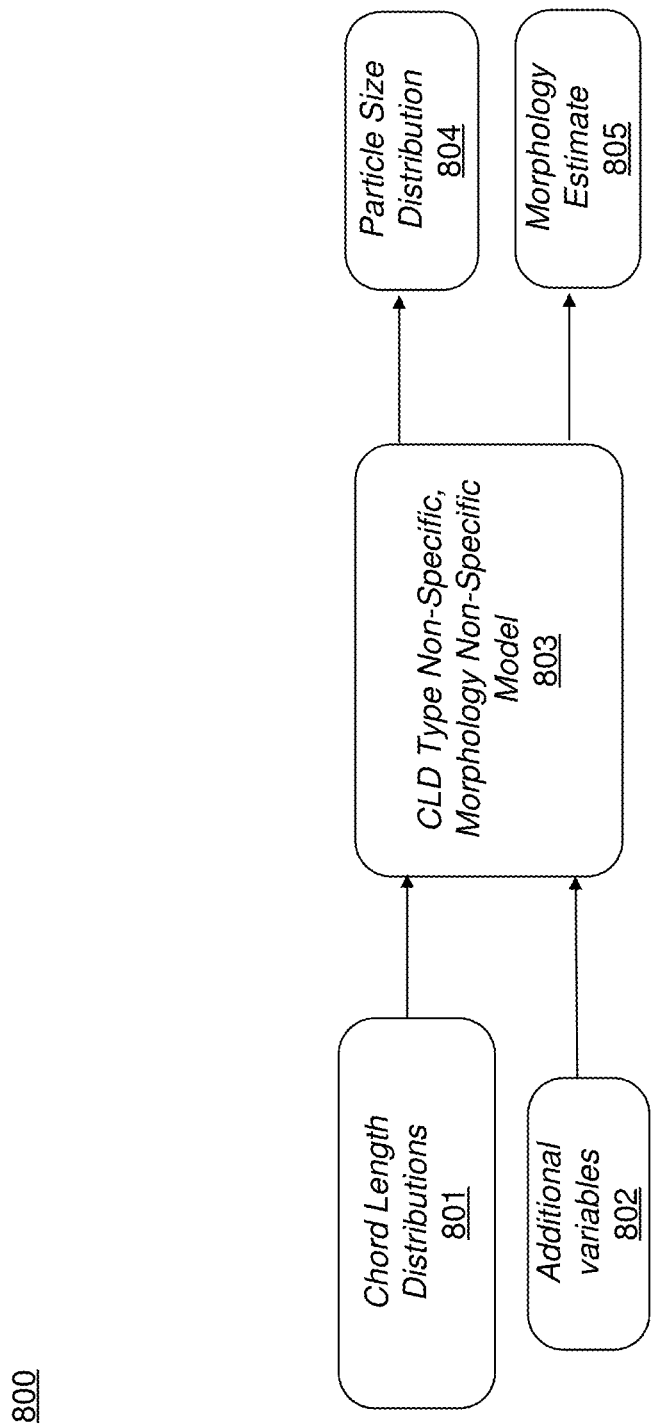
FIG. 8 is a system diagram of a system for generating a PSD and a morphology estimate for a set of particles, in accordance with an embodiment.

FIG. 8 is a system diagram 800 of a system for generating a PSD 804 and a morphology estimate 805 for a set of particles, in accordance with an embodiment. Most of the description of FIG. 4 also applies to FIG. 8. However, unlike the model 403 of FIG. 4, the model 803 of FIG. 8 is not CLD type specific or particle morphology specific. In other words, the model 803 is configured to generate a PSD 804 for a set of particles including particles of any morphology, based on a plurality of CLDs 801 of different types. Therefore, the model 803 can be trained and validated using samples based on sets of particles including particles of any morphology, based on any type of CLD 801. As a result, a computer system can train, validate, and maintain a single model 803 to test any set of particles, which may enable the model to be trained with less data than multiple CLD type specific models. Additionally, as discussed in further detail below with regard to FIGS. 10-14, unlike the model 403 of FIG. 4, the model 803 of FIG. 8 is also configured to generate a morphology estimate 805 for a set of particles.

Figure 9:
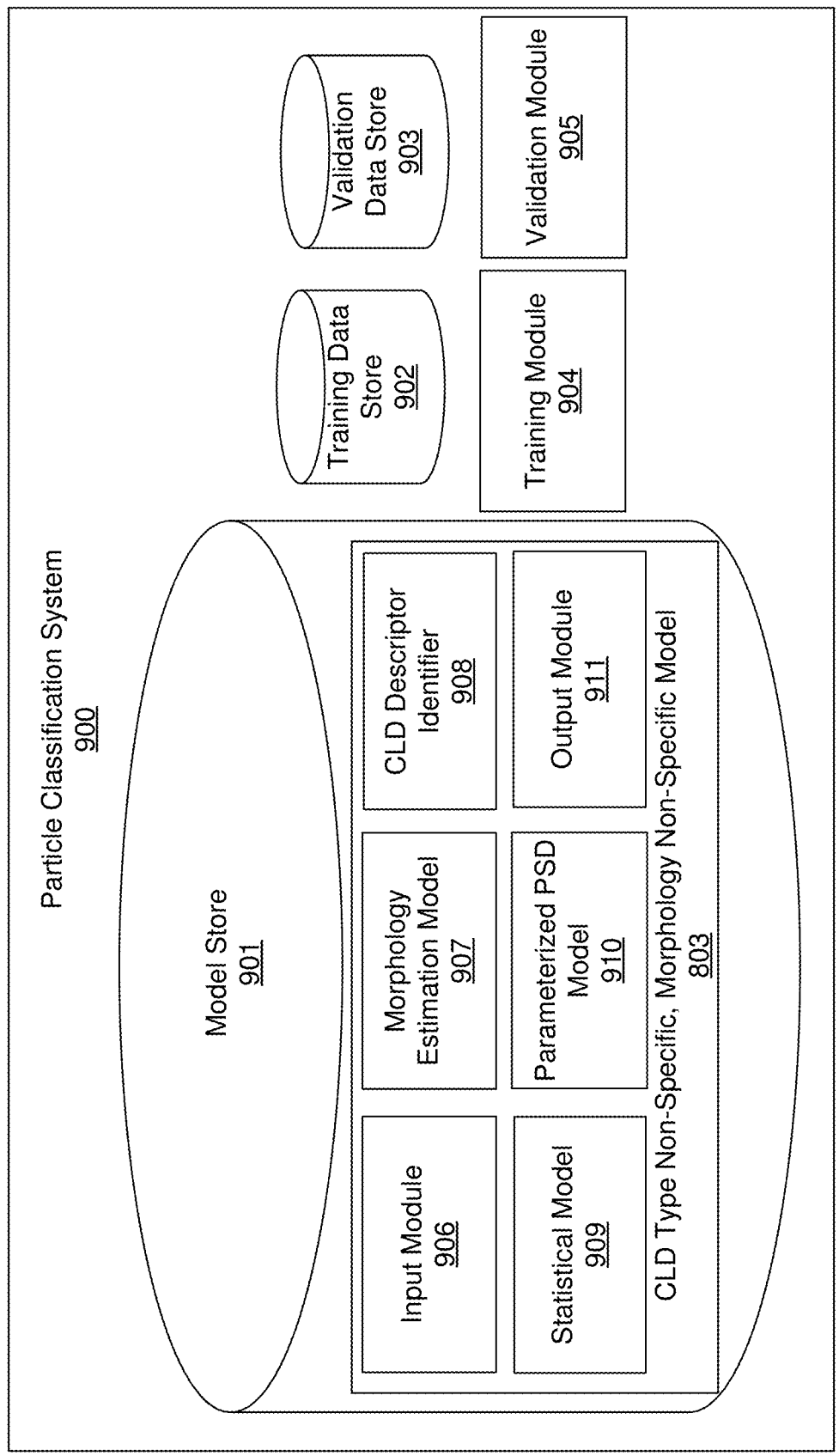
FIG. 9 is a block diagram of a particle classification system that uses the model of FIG. 8 to generate a PSD and a morphology estimate for a set of particles, in accordance with an embodiment.

FIG. 9 is a block diagram of a particle classification system 900 that uses the model 803 to generate a PSD 804 and a morphology estimate 805 for a set of particles, in accordance with an embodiment. As shown in FIG. 9, the particle classification system 900 includes a model store 901, a training data store 902, a validation store 903, a training module 904, and a validation module 905. The model store 901 stores the model 803 of FIG. 8. The model 803 in turn includes an input module 906, a morphology estimation model 907, a CLD descriptor identifier 908, a statistical model 909, a parameterized PSD model 910, and an output module 911. In alternative embodiments, the particle classification system 900 may also include additional modules not depicted herein.

Turning first to the model 803, as noted above, the model 803 includes the input module 906, the morphology estimation model 907, the CLD descriptor identifier 908, the statistical model 909, the parameterized PSD model 910, and the output module 911. The input module 906 accepts inputs to the model. Inputs to the model include a plurality of CLDs of different types for a set of particles, and in some embodiments, additional variables discussed in further detail below with regard to FIGS. 10-13. The morphology estimation model 907 is configured to estimate a morphology for the particles in the set of particles associated with the plurality of different types of CLDs input into the model 803. In some embodiments, the morphology estimation model 907 is configured to estimate a plurality of estimated morphologies for the set of particles. In such embodiments, each estimated morphology of the plurality of estimated morphologies is associated with a fraction that describes the proportion of particles of the set of particles that have the estimated morphology. For example, the morphology estimation model 907 may estimate that 40% of particles in the set of particles comprise a circular morphology, and 60% of particles in the set of particles comprise a platelet morphology. In some embodiments, the morphology estimation model 907 includes one of a fuzzy classification model, a neuro-fuzzy classification model, a random forest model, a decision tree, a clustering algorithm, a neural network, a multi-class logistic regression model, a deep learning model, and a Bayesian model. The CLD descriptor identifier 908 is configured to identify a plurality of descriptors of the plurality of CLDs input into the model 803. In some embodiments, the plurality of descriptors of the plurality of CLDs include one or more moments of the plurality of CLDs. In further embodiments, the plurality of descriptors of the plurality of CLDs can also include a percentage of particles in the set of particles associated with the plurality of CLDs that have a particle size below an average particle size. In certain embodiments, the CLD descriptor identifier 908 is the CLD descriptor identifier 501 discussed above with regard to FIG. 5. The statistical model 909 estimates metrics for a PSD to be output by model 803, based on the plurality of descriptors of the plurality of CLDs. In certain embodiments, the statistical model 909 is the statistical model 502 discussed above with regard to FIG. 5. The parameterized PSD model 910 then generates an estimate of the PSD based on the PSD metrics estimated by the statistical model 909. In certain embodiments, the parameterized PSD model 910 is the parameterized PSD model 503 discussed above with regard to FIG. 5. Finally, the output module 911 outputs the PSD as estimated by the parameterized PSD model 910, and the morphology for the set of particles as estimated by the morphology estimation model 907.

Turning next to the training data store 902, the training data store 902 stores a training dataset. As discussed above with regard to FIG. 4, the training dataset includes a plurality of training samples. Each training sample is associated with a training set of particles, and includes input(s) and a verified output. In embodiments in which the model 803 is trained as a whole, each training sample includes a plurality of CLDs of different types for a training set of particles, in some embodiments additional input variables, and a verified PSD for the training set of particles. In alternative embodiments in which each individual component of the model 803 is separately trained, each training sample is specific to a component of the model 803. Specifically, a training sample for training the morphology estimation model 907 may include one or more inputs for a training set of particles (as discussed in more detail below with regard to FIGS. 10-13) and a verified particle morphology for the training set of particles. On the other hand, a training sample for training the CLD descriptor identifier 908 may include a plurality of CLDs of different types for a training set of particles as an input and a plurality of descriptors of the plurality of CLDs of the training set of particles as a verified output. A training sample for training the statistical model 909 may include a plurality of descriptors for a plurality of CLDs of a training set of particles as an input and PSD metrics for the training set of particles as a verified output. Finally, a training sample for training the parameterized PSD model 910 may include PSD metrics for a PSD of a training set of particles as an input and a PSD of the training set of particles as a verified output.

As noted above, because the model 803 is not CLD type specific or particle morphology specific, the model 803, when trained as a whole, single unit, can be trained using training samples based on particles of any morphology, based on a plurality of types of CLDs. However, as discussed in further detail below with regard to FIGS. 10-14, in some embodiments, the individual components of the model 803 are CLD type specific or particle morphology specific. Specifically, as discussed in further detail below with regard to FIGS. 10-12, in the embodiment of the model 803 depicted in FIGS. 10-12, the CLD descriptor identifier 908, the statistical model 909, and the parameterized PSD model 910 are particle morphology specific. Therefore, in such embodiments, when trained as individual components, the CLD descriptor identifier 908, the statistical model 909, and the parameterized PSD model 910 are trained using training samples based on particles of a specific morphology associated with the component being trained. Similarly, as discussed in further detail below with regard to FIGS. 13-14, in the embodiment of the model 803 depicted in FIGS. 13-14, the CLD descriptor identifier 908 is CLD type specific. Therefore, in such embodiments, when the CLD descriptor identifier 908 is trained as an individual component, the CLD descriptor identifier 908 is trained using training samples including a CLD 801 of the type associated with the CLD descriptor identifier 908.

Similar to the training data store 902, the validation data store 903 includes a plurality of validation samples. Each validation sample is associated with a validation set of particles, and includes input(s) and a verified output. In embodiments in which the model 803 is validated as a whole, each validation sample includes a plurality of CLDs of different types for a validation set of particles, in some embodiments additional input variables, and a verified PSD for the validation set of particles. In alternative embodiments in which each individual component of the model 803 is separately validated, each validation sample is specific to a component of the model 803. Specifically, a validation sample for validation the morphology estimation model 907 may include one or more inputs for a validation set of particles (as discussed in more detail below with regard to FIGS. 10-13) and a verified particle morphology for the validation set of particles. On the other hand, a validation sample for validation of the CLD descriptor identifier 908 may include a plurality of CLDs of different types for a validation set of particles as an input and a plurality of descriptors of the plurality of CLDs for the validation set of particles as a verified output. A validation sample for validation the statistical model 909 may include a plurality of descriptors for a plurality of CLDs of a validation set of particles as an input and PSD metrics for a PSD for the validation set of particles as a verified output. Finally, a validation sample for validation the parameterized PSD model 910 may include PSD metrics for a PSD for a validation set of particles as an input and a PSD for the validation set of particles as a verified output. However, to improve the reliability of validation of the model 403, the validation dataset includes different samples than the training data set.

As noted above, because the model 803 is not CLD type specific or particle morphology specific, the model 803, when validated as a whole, single unit, can be validated using validation samples based on particles of any morphology, based on a plurality of types of CLDs. However, as discussed in further detail below with regard to FIGS. 10-14, in some embodiments, the individual components of the model 803 are CLD type specific or particle morphology specific. Specifically, as discussed in further detail below with regard to FIGS. 11-12, in the embodiment of the model 803 depicted in FIGS. 10-12, the CLD descriptor identifier 908, the statistical model 909, and the parameterized PSD model 910 are particle morphology specific. Therefore, in such embodiments, when validated as individual components, the CLD descriptor identifier 908, the statistical model 909, and the parameterized PSD model 910 are validated using validation samples based on particles of a specific morphology associated with the component being validated. Similarly, as discussed in further detail below with regard to FIGS. 13-14, in the embodiment of the model 803 depicted in FIGS. 13-14, the CLD descriptor identifier 908 is CLD type specific. Therefore, in such embodiments, when the CLD descriptor identifier 908 is validated as an individual component, the CLD descriptor identifier 908 is validated using validation samples including a CLD 801 of the type associated with the CLD descriptor identifier 908.

Turning next to the training module 904, the training module 904 trains the model 803 using the training dataset stored in the training data store 902, to accurately generate a PSD based on a plurality of CLDs of different types input into the input module 906. As discussed above with regard to the training data store 902, in some embodiments the model 803 is trained as a whole, and in alternative embodiments, each individual component of the model 803 is trained separately. The training module 904 is configured to train the model 803 according to one or both of these embodiments. Specifically, to train the model 803, or a component of the model 803, using the training dataset, the input(s) of each training sample from the training dataset are input into the model 803, or the component of the model 803, by the training module 904. The model 803, or the component of the model 803, subsequently generates an output based on those input(s). Then, the training module 904 compares the output generated by the model 803, or the component of the model 803, with the verified output of the training sample. Based on this comparison between the output generated by the model 803, or the component of the model 803, and the verified output of the training sample, the training module 904 may modify the parameters of the model 803, or the component of the model 803, to enable the model 803, or the component of the model 803, to generate more accurate outputs in future uses.

Similar to the training module 904, the validation module 905 validates the model 803 using the validation dataset stored in the validation data store 903, by determining whether the model 803 has been sufficiently trained to accurately generate a PSD based on a plurality of CLDs of different types input into the input module 906. As discussed above, in some embodiments the model 803 is validated as a whole, and in alternative embodiments, each individual component of the model 803 is validated separately. The validation module 905 is configured to validate the model 803 according to one or both of these embodiments. Specifically, to validate the model 803, or a component of the model 803, using the validation dataset, the input(s) of each validation sample from the validation dataset are input into the model 803, or the component of the model 803, by the validation module 905. The model 803, or the component of the model 803, subsequently generates an output based on those input(s). Then, the validation module 905 compares the output generated by the model 803, or the component of the model 803, with the verified output of the validation sample. Based on this comparison between the output generated by the model 803, or the component of the model 803, and the verified output of the validation sample, the validation module 905 determines whether the model 803, or the component of the model 803, should re-enter the training phase, or move on to the testing phase. Specifically, if the validation module 905 determines that a discrepancy between the output generated by the model 803, or the component of the model 803, and the verified output of the validation sample is equal to or less than threshold discrepancy, the model 803, or the component of the model 803, is considered validated, and the model 803, or the component of the model 803, moves on to the testing phase. However, if the validation module 905 determines that a discrepancy between the output generated by the model 803, or the component of the model 803, and the verified output of the validation sample is greater than the threshold discrepancy, the model 803, or the component of the model 803, is not considered to be validated, and re-enters the training phase to undergo further training. Following both training and validation of the model 803 by the training module 904 and the validation module 905, respectively, the model 803 can be tested.

Figure 10:
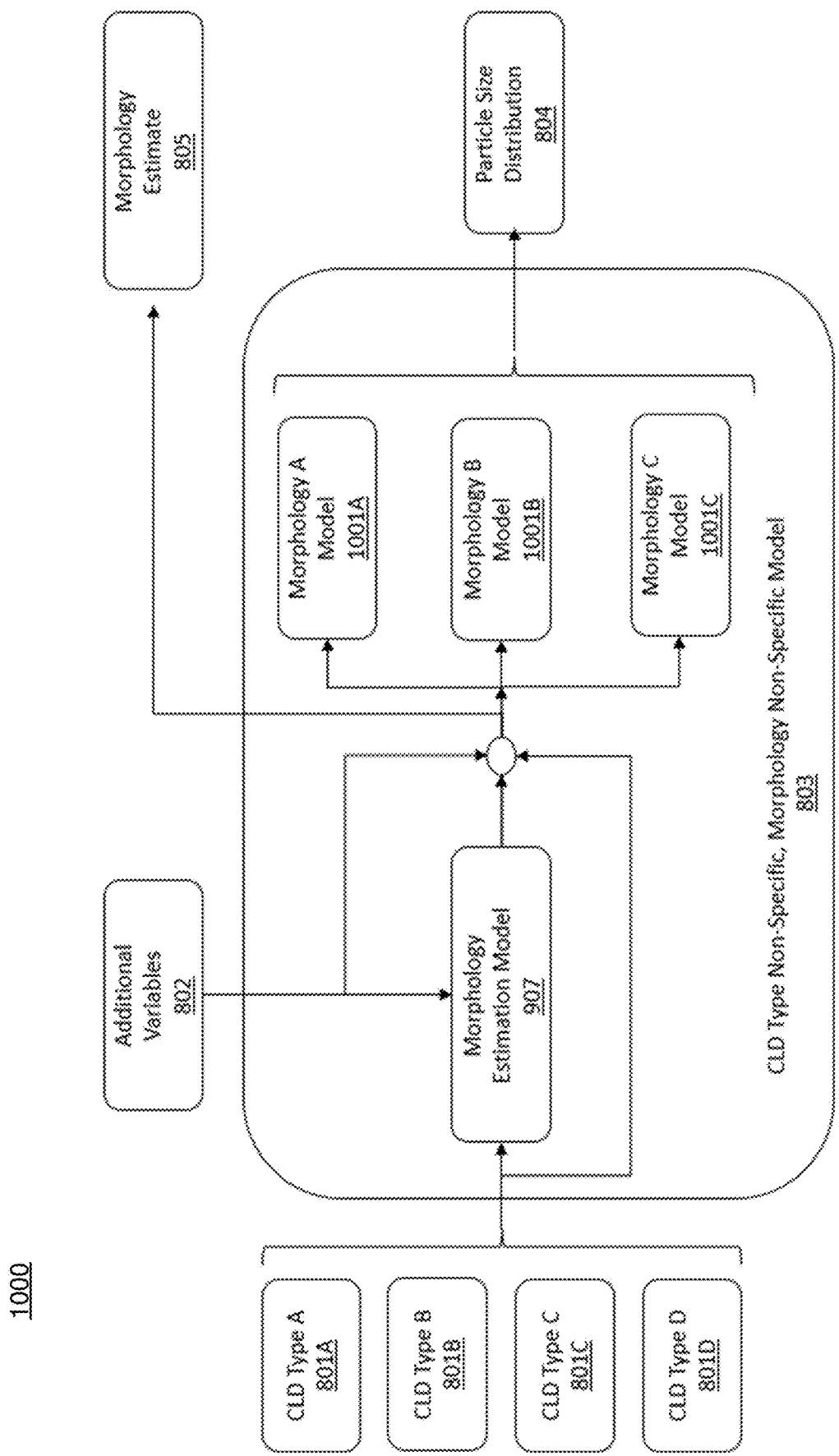
FIG. 10 is a system diagram of the CLD type non-specific, morphology non-specific model of FIG. 8, in accordance with an embodiment.
Figure 11:
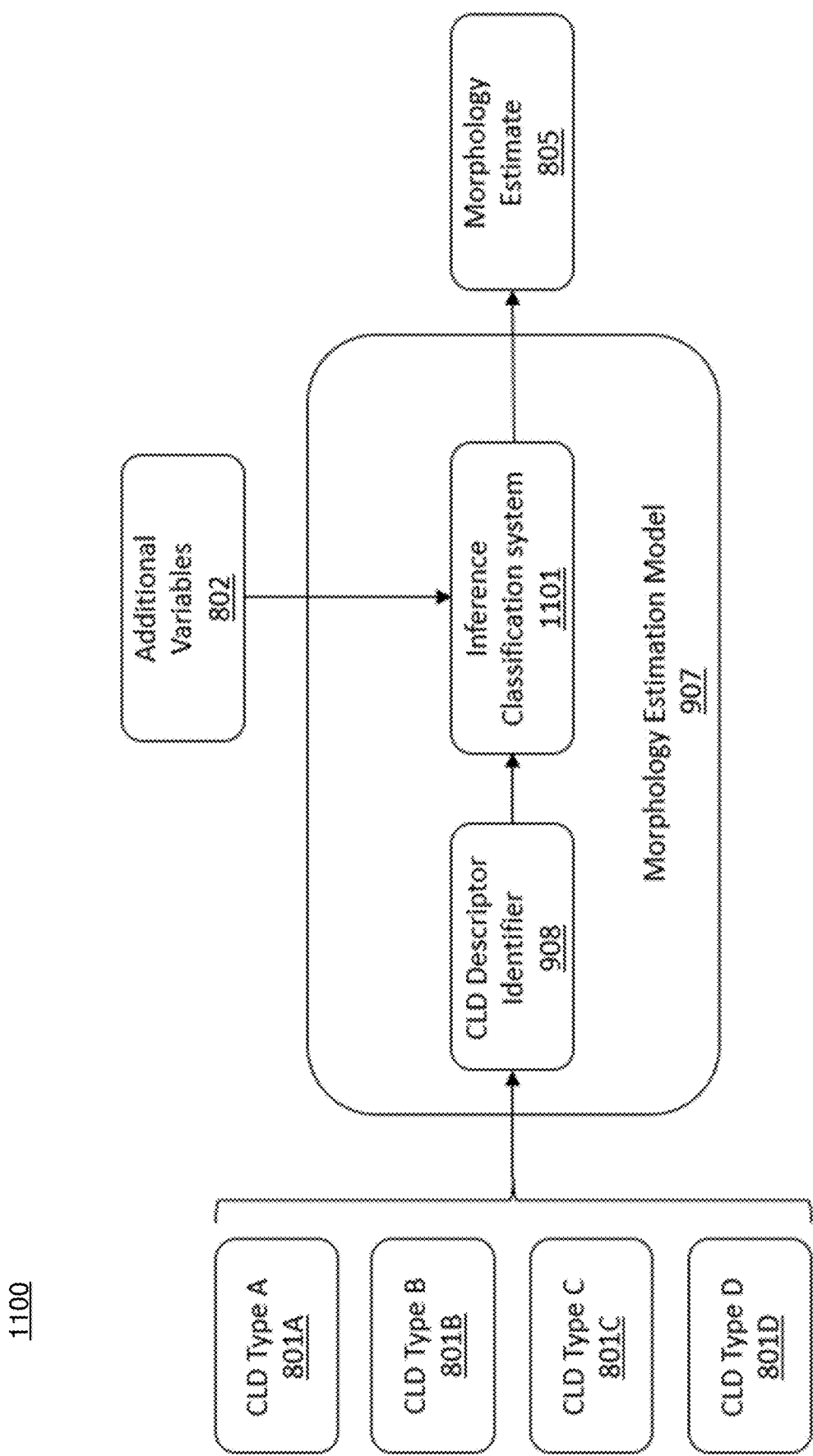
FIG. 11 is a system diagram of the morphology estimation model of FIG. 10, in accordance with an embodiment.
Figure 12:
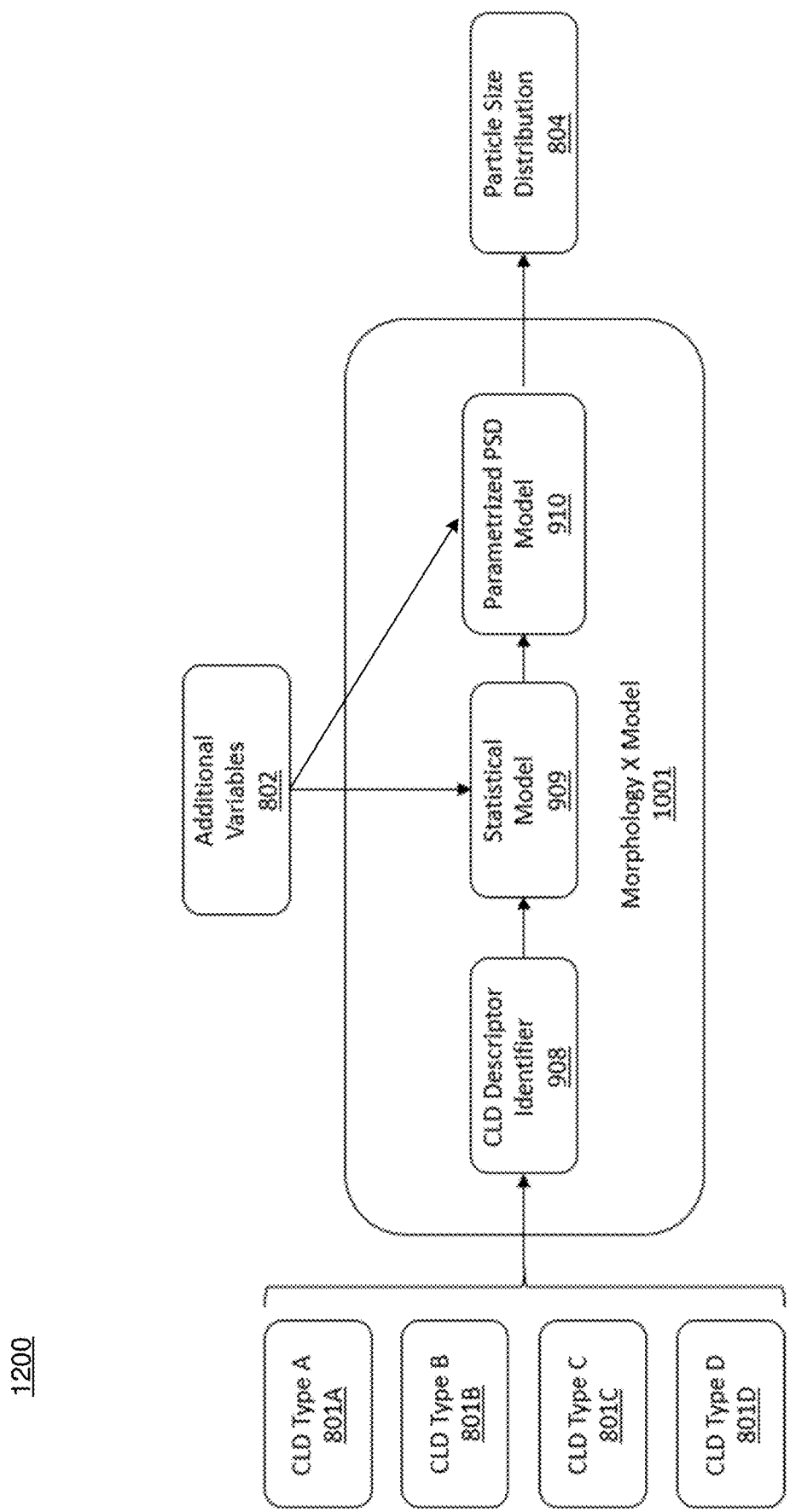
FIG. 12 is a system diagram of a morphology model of FIG. 10, in accordance with an embodiment.
Figure 13:
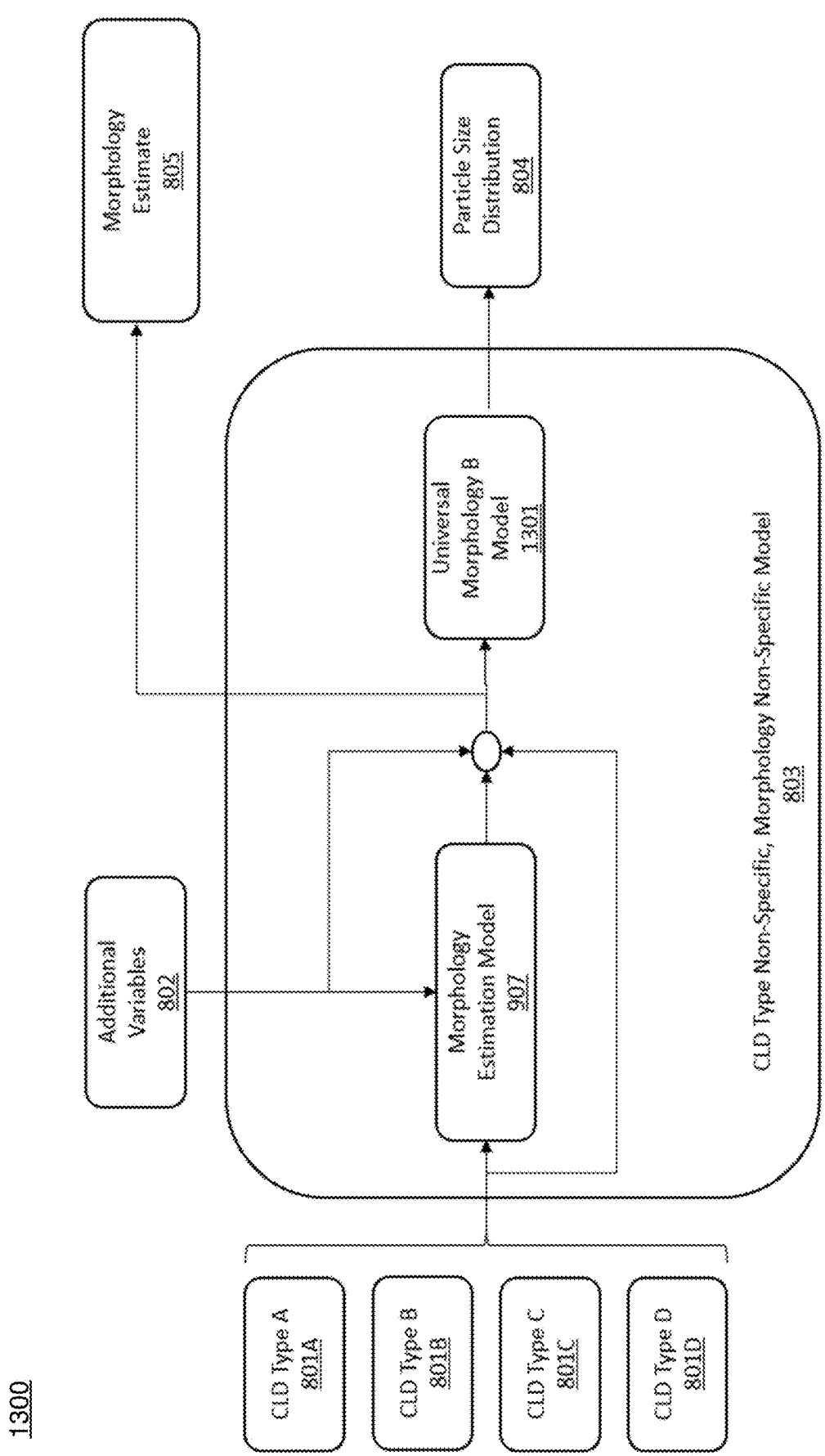
FIG. 13 is a system diagram of the CLD type non-specific, morphology non-specific model of FIG. 8, in accordance with an embodiment.
Figure 14:
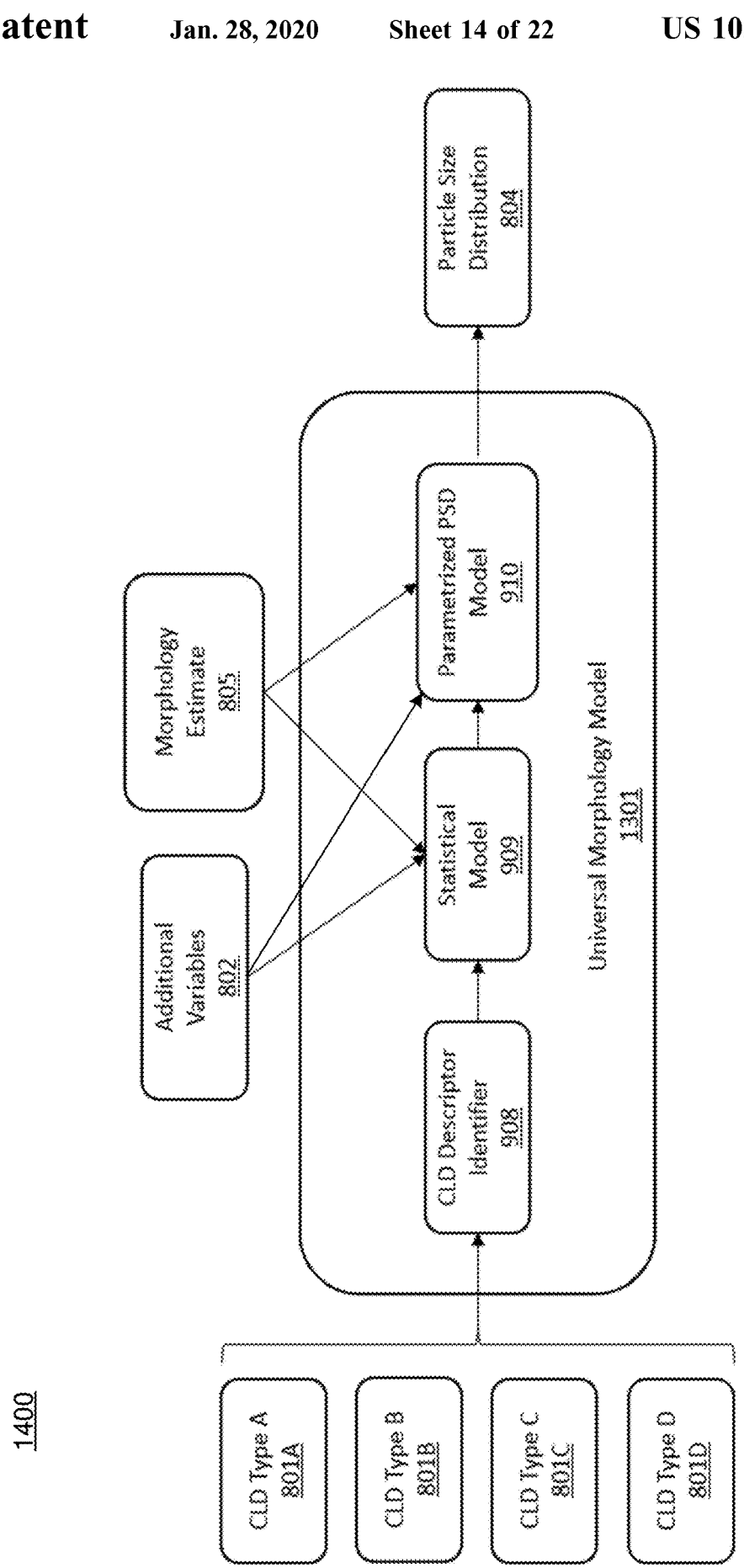
FIG. 14 is a system diagram of the universal morphology model of FIG. 13, in accordance with an embodiment.

Turning back to the system diagram 800 depicted in FIG. 8, to generate a PSD 804 and a morphology estimate 805 for a set of particles based on a plurality of CLDs 801 of different types for the set of particles, the model 803 may be configured according to a plurality of different embodiments. FIGS. 10-12 depict a first exemplar embodiment of the model 803. FIGS. 13-14 depict a second, alternative exemplar embodiment of the model 803. The model 803 may also be configured differently in alternative embodiments not depicted herein.

Turning to a first exemplar embodiment of the model 803, FIG. 10 is a system diagram 1000 of the CLD type non-specific, morphology non-specific model 803 of FIG. 8, in accordance with an embodiment. As shown in FIG. 10, a plurality of CLDs 801 of different types, and in some embodiments, additional variables 802, are input into the model 803, and the model 803 subsequently outputs a PSD 804 and a morphology estimate 805.

As discussed in detail above, the model 803 is both CLD type and particle morphology non-specific. In other words, the model 803 can determine a PSD 804 based on a plurality of CLDs 801 of different types, for a set of particles including particles of any morphology. In one embodiment, four CLD types (referred to herein as CLD type A, CLD type B, CLD type C, and CLD type D) exist. In some embodiments, the model 803 can determine a PSD 804 based on four CLDs 801, each comprising one of the four CLD types. In alternative embodiments, the model 803 can determine a PSD 804 based on any number of CLDs 801 of different types. For example, the model 803 may determine a PSD 804 based on two different types of CLDs 801. This non-specificity of the model 803 to a single CLD type is illustrated in FIG. 10 by depicting a CLD of each type as an input to the model 803. Specifically, FIG. 10 depicts a type A CLD 801A, a type B CLD 801B, a type C CLD 801C, and a type D CLD 801D, each being input into the model 803. Note that this illustration in FIG. 10 does not indicate that a CLD 801 of each type must be input into the model 803 to generate a PSD 804. Rather, this illustration in FIG. 10 indicates that any number of CLDs 801 of different types may be input into the model 803 to generate a PSD 804.

In the embodiment of the model 803 depicted in FIG. 10, the model 803 includes two sequential components. Specifically, the model 803 includes a morphology estimation model 907 and a set of morphology models 1001.

Turning first to the morphology estimation model 907, the morphology estimation model 907 is configured to generate a morphology estimate 805 for a set of particles associated with a plurality of CLDs 801 of different types input into the model 803. The morphology estimation model 907 is configured to generate a discrete morphology estimate 805, and in some embodiments also both a continuous and a discrete morphology estimate 805, for the set of particles associated with the plurality of CLDs 801 of different types input into the model 803. Specifically, the morphology estimation model 907 receives a plurality of CLDs 801 of different types for a set of particles, and outputs a morphology estimate 805. In some embodiments, the morphology estimation model 907 also receives additional variables 802 for the set of particles, and uses the additional variables 802 to generate the morphology estimate 805. The additional variables 802 may include, for example, an in-line particle concentration and/or an in-line video for the set of particles. As noted above, in some embodiments, the morphology estimation model 907 includes one of a fuzzy classification model, a neuro-fuzzy classification model, a random forest model, a decision tree, a clustering algorithm, a neural network, a multi-class logistic regression model, a deep learning model, and a Bayesian model. The morphology estimation model 907 is discussed in further detail below with regard to FIG. 11.

Turning next to the set of morphology models 1001, as depicted in FIG. 10, there are three distinct morphologies models 1001. Each morphology model 1001 is associated with a particular particle morphology, and is configured to generate a PSD 804 based on a plurality of CLDs 801 of different types for a set of particles including particles of the particular particle morphology. For example, a first morphology model, morphology A model 1001A, is associated with particle morphology A, and is configured to generate a PSD 804 based on a plurality of CLDs 801 of different types for a set of particles including particles of the particle morphology A. A second morphology model, morphology B model 1001B, is associated with particle morphology B, and is configured to generate a PSD 804 based on a plurality of CLDs 801 of different types for a set of particles including particles of the particle morphology B. A third morphology model, morphology C model 1001C, is associated with particle morphology C, and is configured to generate a PSD 804 based on a plurality of CLDs 801 of different types for a set of particles including particles of the particle morphology C. In some embodiments, each morphology model 1001 is configured to generate a PSD 804 based on a single CLD 801 of the plurality of CLDs 801 for a set of particles. For example, a morphology model 1001 may generate a PSD 804 based on a single CLD 801 of type A for a set of particles. This ability of the morphology model 1001 to generate a PSD 804 based on a single CLD 801 improves the computational efficiency of PSD estimation. As discussed above, a nearly infinite number of different particle morphologies exist. Therefore, the model 803 may include any number of distinct morphology models, each associated with a different particle morphology, and configured to generate a PSD 804 based on a plurality of CLDs 801 of different types for a set of particles including particles of the associated particle morphology. In some embodiments, each morphology model 1001 also uses additional variables 802 to generate the PSD 804. These additional variables 802 are discussed in further detail below with regard to FIG. 12.

The appropriate morphology model 1001 is selected from the set of morphology models 1001 for use in generating a PSD 804 based on the morphology estimate 805 output by the morphology estimation model 907. For example, if the morphology estimate 805 generated by the morphology estimation model 907 indicates that a set of particles associated with a plurality of CLDs 801 input into the morphology estimation model 907 includes particles of morphology B, then the morphology model B 1001B is used to generate a PSD 804. Alternatively, if the morphology estimate 805 generated by the morphology estimation model 907 indicates that the set of particles associated with the plurality of CLDs 801 input into the morphology estimation model 907 includes particles of morphology C, then the morphology model C 1001C is used to generate a PSD 804.

As discussed in further detail below with regard to FIG. 12, in some embodiments, each of the morphology models 1001 includes the same constituent components. However, as also discussed in further detail below, the morphology models 1001 and/or the constituent components of the morphology models 1001 may include different parameters as a result of being trained using different training datasets and being validated using different validation datasets. More specifically, the morphology models 1001 and/or the constituent components of the morphology models 1001 may include different parameters due to being trained using training samples based on training sets of particles including particles of different particle morphologies, due to being validated using validation samples based on validation sets of particles including particles of different particle morphologies. As a result of this difference in parameters between morphology models 1001, the PSDs 804 output by the morphology models 1001 may differ.

As discussed above with regard to FIG. 9, prior to using the model 803 for testing, the model 803 is trained and validated. In some embodiments, the model 803 is trained and validated as a single unit. In such embodiments in which the model 803 is trained and validated as a single unit, each training sample in the plurality of training samples that includes the training dataset includes a plurality of CLDs 801 of different types for a training set of particles including particles of any morphology as an input, and a PSD 804 for the training set of particles as a verified output. The plurality of CLDs 801 are input into the model 803, and the model 803 subsequently outputs a PSD 804 based on the plurality of CLDs 801. Then, the PSD 804 output by the model 803 is compared with the verified PSD 804 of the training sample. Based on this comparison between the PSD 804 output by the model 803 and the verified PSD 804 of the training sample, the parameters of the model 803 are modified to enable the model 803 to generate more accurate PSDs 804 in future uses.

Similarly, in such embodiments in which the model 803 is validated as a single unit, each validation sample in the plurality of validation samples that includes the validation dataset includes a plurality of CLDs 801 of different types for a validation set of particles including particles of any morphology as an input, and a PSD 804 for the validation set of particles as a verified output. The plurality of CLDs 801 are input into the model 803, and the model 803 subsequently outputs a PSD 804 based on the plurality of CLDs 801. Then, the PSD 804 output by the model is compared with the verified PSD 804 of the validation sample. Based on this comparison between the PSD 804 output by the model 803 and the verified PSD 804 of the validation sample, the model 803 is considered validated, and the model moves on to the testing phase, or the model 803 is not considered to be validated, and re-enters the training phase to undergo further training.

In alternative embodiments, the model 803 is not trained and validated as a single unit, but rather, each individual component of the model 803 is separately trained and separately validated. Specifically, in alternative embodiments, the morphology estimation model 907 and each distinct morphology model 1001 are separately trained and validated using unique training and validation datasets, respectively. In such embodiments, the morphology estimation model 907 is trained and validated using a first training and validation dataset, respectively, and each morphology model 1001 is trained and validated using its own training and validation dataset, respectively.

Because the morphology estimation model 907 is configured to receive a plurality of CLDs 801 of different types for a set of particles including particles of any morphology, each training sample in the training dataset for the morphology estimation model 907 includes, as an input, a plurality of CLDs 801 of different types for a training set of particles including any morphology, and, as a verified output, a morphology for the training set of particles. In some embodiments, each training sample in the training dataset also includes one or more of an in-line particle concentration and an in-line particle video as inputs. The plurality of CLDs 801 of different types, and in some embodiments one or more of the in-line particle concentration and the in-line particle video, are input into the morphology estimation model 907, and the morphology estimation model 907 subsequently outputs an estimated morphology 805 based on the plurality of CLDs 801, and in some embodiments one or more of the in-line particle concentration and the in-line particle video. Then, the estimated morphology 805 output by the morphology estimation model 907 is compared with the verified morphology of the training sample. Based on this comparison between the estimated morphology 805 output by the morphology estimation model 907 and the verified morphology of the training sample, the parameters of the morphology estimation model 907 are modified to enable the morphology estimation model 907 to generate more accurate estimated morphologies 805 in future uses.

Similarly, in such embodiments in which the morphology estimation model 907 is validated as a single unit, each validation sample in the plurality of validation samples that includes the validation dataset includes a plurality of CLDs 801 of different types for a validation set of particles including any morphology as an input, and a morphology for the validation set of particles as a verified output. In some embodiments, each training sample in the training dataset also includes one or more of an in-line particle concentration and an in-line particle video as inputs. The plurality of CLDs 801, and in some embodiments one or more of the in-line particle concentration and the in-line particle video, are input into the morphology estimation model 907, and the morphology estimation model 907 subsequently outputs an estimated morphology 805 based on the plurality of CLDs 801, and in some embodiments one or more of the in-line particle concentration and the in-line particle video. Then, the estimated morphology 805 output by the model is compared with the verified morphology of the validation sample. Based on this comparison between the estimated morphology 805 output by the morphology estimation model 907 and the verified morphology of the validation sample, either the morphology estimation model 907 is considered validated, and the model moves on to the testing phase, or the morphology estimation model 907 is not considered to be validated, and re-enters the training phase to undergo further training.

In embodiments in which the morphology estimation model 907 is trained and validated as a single unit, in general, the morphology estimation model 907 includes a function representing a relation between a plurality of CLDs 801 of different types for a set of particles and the morphology for the set of particles, the function based on a training dataset for the morphology estimation model 907.

Contrary to the morphology estimation model 907, because each morphology model 1001 is specific to a particular particle morphology, each morphology model 1001 is trained with a distinct training dataset including a plurality of training samples, each training sample including, as an input, a plurality of CLDs 801 of different types for a training set of particles including particles of the particle morphology associated with the morphology model 1001 being trained, and, as a verified output, a PSD 804 for the training set of particles. The plurality of CLDs 801 are input into the morphology model 1001, and the morphology model 1001 subsequently outputs a PSD 804 based on the plurality of CLDs 801. Then, the PSD 804 output by the morphology model 1001 is compared with the verified PSD 804 of the training sample. Based on this comparison between the PSD 804 output by the morphology model 1001 and the verified PSD 804 of the training sample, the parameters of the morphology model 1001 are modified to enable the morphology model 1001 to generate more accurate PSDs 804 in future uses.

Similarly, in such embodiments in which the morphology model 1001 is validated as a single unit, each validation sample in the plurality of validation samples that includes the validation dataset includes, as an input, a plurality of CLDs 801 of different types for a validation set of particles including particles of the particle morphology associated with the morphology model 1001 being validated, and as a verified output, a PSD 804 for the validation set of particles. The plurality of CLDs 801 are input into the morphology model 1001, and the morphology model 1001 subsequently outputs a PSD 804 based on the plurality of CLDs 801. Then, the PSD 804 output by the model is compared with the verified PSD 804 of the validation sample. Based on this comparison between the PSD 804 output by the morphology model 1001 and the verified PSD 804 of the validation sample, either the morphology model 1001 is considered validated, and the model moves on to the testing phase, or the morphology model 1001 is not considered to be validated, and re-enters the training phase to undergo further training. This differential training and validation of each of the morphology models 1001 may cause parameters to differ between morphology models 1001, and thus may cause the output PSDs 804 to differ between morphology models 1001.

FIG. 11 is a system diagram 1100 of a morphology estimation model 907, in accordance with an embodiment. The morphology estimation model 907 is configured to generate a discrete, and in some embodiments both a discrete and a continuous, morphology estimate 805 for a set of particles associated with a plurality of CLDs 801 of different types input into the model 803.

The morphology estimation model 907 receives a plurality of CLDs 801 of different types for a set of particles, and outputs a morphology estimate 805. In some embodiments, the morphology estimation model 907 also receives additional variables 802 for the set of particles, and uses the additional variables 802 to generate the morphology estimate 805. The additional variables 802 may include, for example, an in-line particle concentration and/or an in-line video for the set of particles. As noted above, in some embodiments, the morphology estimation model 907 includes one of a fuzzy classification model, a neuro-fuzzy classification model, a random forest model, a decision tree, a clustering algorithm, a neural network, a multi-class logistic regression model, a deep learning model, and a Bayesian model.

The morphology estimation model 907 can determine a morphology estimate 805 based on a plurality of CLDs 801 of different types. In one embodiment, four CLD types (referred to herein as CLD type A, CLD type B, CLD type C, and CLD type D) exist. In some embodiments, the morphology estimation model 907 can determine a morphology estimate 805 based on four CLDs 801, each comprising one of the four CLD types. In alternative embodiments, the morphology estimation model 907 can determine a morphology estimate 905 based on any number of CLDs 801 of different types. For example, the morphology estimation model 907 may determine a morphology estimate 805 based on two different types of CLDs 801. This non-specificity of the morphology estimation model 907 to a single CLD type is illustrated in FIG. 11 by depicting a CLD of each type as an input to the morphology estimation model 907. Specifically, FIG. 11 depicts a type A CLD 801A, a type B CLD 801B, a type C CLD 801C, and a type D CLD 801D, each being input into the morphology estimation model 907. Note that this illustration in FIG. 11 does not indicate that a CLD 801 of each type must be input into the morphology estimation model 907 to generate a morphology estimate 805. Rather, this illustration in FIG. 11 indicates that any number of CLDs 801 of different types may be input into the morphology estimation model 907 to generate a morphology estimate.

In the embodiment of the model 803 depicted in FIG. 10, the model 803 includes two sequential components. Specifically, the model 803 includes CLD descriptor identifier 908 and an inference classification system 1101. The CLD descriptor identifier 908 is configured to identify a plurality of descriptors of a CLD 801. Specifically, the CLD descriptor identifier 908 receives the plurality of CLDs 801 (in some embodiments a single CLD 801) and outputs a plurality of descriptors of the plurality of CLDs 801. In some embodiments, the plurality of descriptors of the plurality of CLDs 801 that are output by the CLD descriptor identifier 908 include one or more moments of the plurality of CLDs 801. In further embodiments, the plurality of descriptors of the plurality of CLDs 801 that are output by the CLD descriptor identifier 908 can also include a percentage of particles in the set of particles associated with the plurality of CLDs 801 that have a particle size below an average particle size.

The inference classification system 1101 is configured to generate a morphology estimate 805 based on the plurality of CLD descriptors identified by the CLD descriptor identifier 908 as well as the additional variables 802.

FIG. 12 is a system diagram 1200 of a morphology model 1001 of FIG. 10, in accordance with an embodiment. As discussed above with regard to FIG. 10, the model 803 includes a plurality of distinct morphology models 1001. Each morphology model 1001 is associated with a particular particle morphology, and is configured to generate a PSD 804 based on a plurality of CLDs 801 of different types for a set of particles including particles of the particular particle morphology. For example, a first morphology model, morphology A model 1001A, is associated with particle morphology A, and is configured to generate a PSD 804 based on a plurality of CLDs 801 of different types for a set of particles including particles of the particle morphology A. However, in some embodiments, each morphology model 1001 includes the same constituent components, regardless of the particle morphology with which it is associated. Therefore, the system diagram 1200 of the morphology model 1001 depicted in FIG. 12 applies to each of the distinct morphology models 1001 depicted in FIG. 10. To indicate this generalizability of the system diagram 1200 of the morphology model 1001 depicted in FIG. 12 to each of the distinct morphology models 1001 depicted in FIG. 10, the morphology model 1001 depicted in FIG. 12 is labeled "morphology X model 1001."

As seen in FIG. 12, a plurality of CLDs 801 of different types, and in some embodiments additional variables 802, are input into the morphology X model 1001, and the morphology X model 1001 subsequently outputs a PSD 804. As discussed above with regard to FIG. 10, the model 803, and the morphology X model 1001, are CLD type non-specific. In other words, the morphology X model 1001 can determine a PSD 804 based on a plurality of CLDs 801 of different types. This non-specificity of the morphology X model 1001 to a single CLD type is illustrated in FIG. 12 by depicting a CLD of each type as an input to the morphology X model 1001. Specifically, FIG. 12 depicts a type A CLD 801A, a type B CLD 801B, a type C CLD 801C, and a type D CLD 801D, each being input into the morphology X model 1001. Note that this illustration in FIG. 12 does not indicate that a CLD 801 of each type must be input into the morphology X model 1001 to generate a PSD 804. Rather, this illustration in FIG. 12 indicates that any number of CLDs 801 of different types may be input into the morphology X model 1001 to generate a PSD 804. For example, in some embodiments, the morphology X model 1001 generates a PSD 804 based on a single CLD 801. For example, a morphology model 1001 may generate a PSD 804 based on a single CLD 801 of type D.

However, as discussed in detail above, unlike the model 803, the morphology X model 1001 is not morphology non-specific. Specifically, as discussed above, each morphology X model 1001 is associated with a particular particle morphology, and is configured to generate a PSD 804 based on a plurality of CLDs 801 of different types for a set of particles including particles of the particular particle morphology. Therefore, the plurality of CLDs 801 input into the morphology X model 1001 should be for a set of particles including particles of the morphology associated with the morphology X model 1001.

In the embodiment of the morphology X model 1001 depicted in FIG. 12, the morphology X model 1001 includes three separate, sequential components. Specifically, the morphology X model 1001 includes a CLD descriptor identifier 908, a statistical model 909, and a parameterized PSD model 910.

Turning first to the CLD descriptor identifier 908, the CLD descriptor identifier 908 receives the plurality of CLDs 801 (in some embodiments a single CLD 801) and outputs a plurality of descriptors of the plurality of CLDs 801. In some embodiments, the plurality of descriptors of the plurality of CLDs 801 that are output by the CLD descriptor identifier 908 include one or more moments of the plurality of CLDs 801. In further embodiments, the plurality of descriptors of the plurality of CLDs 801 that are output by the CLD descriptor identifier 908 can also include a percentage of particles in the set of particles associated with the plurality of CLDs 801 that have a particle size below an average particle size.

Turning next to the statistical model 909, the statistical model 909 receives the plurality of descriptors of the plurality of CLDs 801 output by the CLD descriptor identifier 908. In some embodiments, the statistical model 909 also receives additional variables 802. The additional variables 802 can include, for example, a slurry concentration for the set of particles associated with the plurality of CLDs 801. The statistical model 909 then estimates metrics for the PSD 804 based on the plurality of identified descriptors, and in some embodiments, the additional variables 802. In certain embodiments, the statistical model includes a regression model that is configured to perform regression analysis to estimate the metrics for the PSD 804.

Turning finally to the parameterized PSD model 910, the parameterized PSD model 910 receives the PSD metrics output by the statistical model 909, and generates an estimate of the PSD 804 based on the PSD metrics. This estimate of the PSD 804 is subsequently output by the morphology X model 1001. In some embodiments, the parameterized PSD model 910 includes a neural network model.

As discussed above with regard to FIG. 10, prior to using the morphology X model 1001 for testing, the morphology X model 1001 is trained and validated. In some embodiments, the morphology X model 1001 is trained and validated as a single unit. Such embodiments are discussed above with regard to FIG. 10.

In alternative embodiments, the morphology X model 1001 is not trained and validated as a single unit, but rather, each individual component of the morphology X model 1001 is separately trained and separately validated. Specifically, in alternative embodiments, each of the CLD descriptor identifier 908, the statistical model 909, and the parameterized PSD model 910 are separately trained and validated using unique training and validation datasets, respectively. Specifically, in such embodiments, the CLD descriptor identifier 908 is trained and validated using a first training and validation dataset, respectively, the statistical model 909 is trained and validated using a second training and validation dataset, respectively, and the parameterized PSD model 910 is trained and validated using a third training and validation dataset, respectively. As discussed above, with regard to FIG. 10, because each morphology X model 1001 is specific to a particular particle morphology, for a given morphology X model 1001, each training sample in the training dataset for each of the three components of the morphology X model 1001, and each validation sample in the validation dataset for each of the three components of the morphology X model 1001, is based on particles including the particle morphology associated with the morphology X model 1001. However, because the morphology X model 1001 is not specific to a CLD type, for a given morphology X model 1001, each training sample in the training dataset for each of the three components of the morphology X model 1001, and each validation sample in the validation dataset for each of the three components of the morphology X model 1001, may be based on a plurality of CLDs 801 of different types.

Each training sample in the plurality of training samples that includes the training dataset for the CLD descriptor identifier 908 includes a plurality of CLDs 801 of different types as an input and a plurality of descriptors of the plurality of CLDs 801 of different types as a verified output. The plurality of CLDs 801 are input into the CLD descriptor identifier 908, and the CLD descriptor identifier 908 subsequently outputs a plurality of descriptors based on the plurality of CLDs 801. Then, the plurality of descriptors output by the CLD descriptor identifier 908 is compared with the verified plurality of descriptors of the training sample. Based on this comparison between the plurality of descriptors output by the CLD descriptor identifier 908 and the verified plurality of descriptors of the training sample, the parameters of the CLD descriptor identifier 908 are modified to enable the CLD descriptor identifier 908 to generate more accurate descriptors in future uses. Similarly, in such embodiments in which the CLD descriptor identifier 908 is validated as a single unit, each validation sample in the plurality of validation samples that includes the validation dataset includes a plurality of CLDs 801 of different types as an input and a plurality of descriptors as a verified output. The plurality of CLDs 801 are input into the CLD descriptor identifier 908, and the CLD descriptor identifier 908 subsequently outputs a plurality of descriptors based on the plurality of CLDs 801. Then, the plurality of descriptors output by the model is compared with the verified plurality of descriptors of the validation sample. Based on this comparison between the plurality of descriptors output by the CLD descriptor identifier 908 and the verified plurality of descriptors of the validation sample, either the CLD descriptor identifier 908 is considered validated, and the model moves on to the testing phase, or the CLD descriptor identifier 908 is not considered to be validated, and re-enters the training phase to undergo further training.

Similarly, each training sample in the plurality of training samples that includes the training dataset for the statistical model 909 includes a plurality of descriptors for the plurality of CLDs 801 as an input and PSD metrics for the PSD 804 as a verified output. In some embodiments, each training sample in the training dataset also includes a slurry concentration as an input. The plurality of descriptors, and in some embodiments, the slurry concentration, are input into the statistical model 909, and the statistical model 909 subsequently outputs PSD metrics based on the plurality of descriptors, and in some embodiments the slurry concentration. Then, the PSD metrics output by the statistical model 909 are compared with the verified PSD metrics of the training sample. Based on this comparison between the PSD metrics output by the statistical model 909 and the verified PSD metrics of the training sample, the parameters of the statistical model 909 are modified to enable the statistical model 909 to generate more accurate PSD metrics in future uses. Similarly, in such embodiments in which the statistical model 909 is validated as a single unit, each validation sample in the plurality of validation samples that includes the validation dataset includes a plurality of descriptors for the plurality of CLDs 801 as an input and PSD metrics for the PSD 804 as a verified output. In some embodiments, each validation sample in the validation dataset also includes a slurry concentration as an input. The plurality of descriptors, and in some embodiments the slurry concentration, are input into the statistical model 909, and the statistical model 909 subsequently outputs PSD metrics based on the plurality of descriptors, and in some embodiments the slurry concentration. Then, the PSD metrics output by the model are compared with the verified PSD metrics of the validation sample. Based on this comparison between the PSD metrics output by the statistical model 909 and the verified PSD metrics of the validation sample, either the statistical model 909 is considered validated, and the model moves on to the testing phase, or the statistical model 909 is not considered to be validated, and re-enters the training phase to undergo further training.

Similarly, for the parameterized PSD model 910, each training sample in the plurality of training samples that includes the training dataset for the parameterized PSD model 910 includes PSD metrics for the PSD 804 as an input and a PSD 804 as a verified output. The PSD metrics are input into the parameterized PSD model 910, and the parameterized PSD model 910 subsequently outputs a PSD 804 based on the PSD metrics. Then, the PSD 804 output by the parameterized PSD model 910 is compared with the verified PSD 804 of the training sample. Based on this comparison between the PSD 804 output by the parameterized PSD model 910 and the verified PSD 804 of the training sample, the parameters of the parameterized PSD model 910 are modified to enable the parameterized PSD model 910 to generate a more accurate PSD 804 in future uses. Similarly, in such embodiments in which the parameterized PSD model 910 is validated as a single unit, each validation sample in the plurality of validation samples that includes the validation dataset includes PSD metrics for the PSD 804 as an input and a PSD 804 as a verified output. The PSD metrics are input into the parameterized PSD model 910, and the parameterized PSD model 910 subsequently outputs a PSD 804 based on the PSD metrics. Then, the PSD 804 output by the model is compared with the verified PSD 804 of the validation sample. Based on this comparison between the PSD 804 output by the parameterized PSD model 910 and the verified PSD 804 of the validation sample, either the parameterized PSD model 910 is considered validated, and the model moves on to the testing phase, or the parameterized PSD model 910 is not considered to be validated, and re-enters the training phase to undergo further training.

In embodiments in which the descriptor identifier 908 is trained and validated as a single unit, in general the descriptor identifier 908 includes a function representing a relation between a chord length distribution for a set of particles and a plurality of identified descriptors of the chord length distribution for the set of particles, the function based on a training dataset for the descriptor identifier 908. In embodiments in which the statistical model 909 is trained and validated as a single unit, in general the statistical model 909 includes a function representing a relation between a plurality of identified descriptors for a plurality of CLDs 801 and PSD metrics for a PSD 804, the function based on a training dataset for the statistical model 802. Similarly, in embodiments in which the parameterized PSD model 910 is trained and validated as a single unit, in general the parameterized PSD model 910 includes a function representing a relation between PSD metrics for a PSD 804 and the PSD 804, the function based on a training dataset for the parameterized PSD model 910.

Turning to a second exemplar embodiment of the model 803, FIG. 13 is a system diagram 1300 of the CLD type non-specific, morphology non-specific model 803 of FIG. 8, in accordance with an embodiment. As shown in FIG. 13, a plurality of CLDs 801 of different types, and in some embodiments, additional variables 802, are input into the model 803, and the model 803 subsequently outputs a PSD 804 and a morphology estimate 805.

As discussed in detail above, the model 803 is both CLD type and particle morphology non-specific. Therefore, the model 803 can determine a PSD 804 based on a plurality of CLDs 801 of different types. This non-specificity of the model 803 to a single CLD type is illustrated in FIG. 13 by depicting a CLD of each type as an input to the model 803. Specifically, FIG. 13 depicts a type A CLD 801A, a type B CLD 801B, a type C CLD 801C, and a type D CLD 801D, each being input into the model 803. Note that this illustration in FIG. 13 does not indicate that a CLD 801 of each type must be input into the model 803 to generate a PSD 804. Rather, this illustration in FIG. 13 indicates that any number of CLDs 801 of different types may be input into the model 803 to generate a PSD 804.

In the embodiment of the model 803 depicted in FIG. 13, the model 803 includes two sequential components. Specifically, the model 803 includes a morphology estimation model 907 and a universal morphology model 1301.

Turning first to the morphology estimation model 907, the morphology estimation model 907 is configured to generate a morphology estimate 805 for a set of particles associated with a plurality of CLDs 801 of different types input into the model 803. The morphology estimation model 907 is configured to generate a continuous morphology estimate 805, and in some embodiments also both a continuous and a discrete morphology estimate 805, for the set of particles associated with the plurality of CLDs 801 of different types input into the model 803. Specifically, the morphology estimation model 907 receives a plurality of CLDs 801 of different types for a set of particles, and outputs a morphology estimate 805. In some embodiments, the morphology estimation model 907 also receives additional variables 802 for the set of particles, and uses the additional variables 802 to generate the morphology estimate 805. The additional variables 802 may include, for example, an in-line particle concentration and/or an in-line video for the set of particles. As noted above, in some embodiments, the morphology estimation model 907 includes one of a fuzzy classification model, a neuro-fuzzy classification model, a random forest model, a decision tree, a clustering algorithm, a neural network, a multi-class logistic regression model, a deep learning model, and a Bayesian model. The morphology estimation model 907 is discussed in further detail above with regard to FIG. 11.

Turning next to the universal morphology model 1301, the universal morphology model 1301 is configured to generate an estimate of a PSD 804 for a set of particles, based on a plurality of descriptors of a plurality of CLDs 801 of different types for the set of particles and on a morphology estimate 805 for the set of particles. Specifically, the universal morphology model 1301 receives a plurality of descriptors of a plurality of CLDs 801 of different types for a set of particles including particles of any morphology from the set of CLD descriptor identifiers 908 and a morphology estimate 805 for the set of particles from the morphology estimation model 907, and estimates a PSD 804 for the set of particles. In some embodiments, the universal morphology model 1301 also receives additional variables 802 for the set of particles, and uses the additional variables 802 to generate the PSD 804. The additional variables 802 may include, for example, a slurry concentration for the set of particles. The components of the universal morphology model 1301 are discussed in detail below with regard to FIG. 14.

As discussed above with regard to FIG. 9, prior to using the model 803 for testing, the model 803 is trained and validated. In some embodiments, the model 803 is trained and validated as a single unit. In such embodiments in which the model 803 is trained and validated as a single unit, each training sample in the plurality of training samples that includes the training dataset includes a plurality of CLDs 801 of different types for a training set of particles including particles of any morphology as an input, and a PSD 804 for the training set of particles as a verified output. The plurality of CLDs 801 are input into the model 803, and the model 803 subsequently outputs a PSD 804 based on the plurality of CLDs 801. Then, the PSD 804 output by the model 803 is compared with the verified PSD 804 of the training sample. Based on this comparison between the PSD 804 output by the model 803 and the verified PSD 804 of the training sample, the parameters of the model 803 are modified to enable the model 803 to generate more accurate PSDs 804 in future uses. Similarly, in such embodiments in which the model 803 is validated as a single unit, each validation sample in the plurality of validation samples that includes the validation dataset includes a plurality of CLDs 801 of different types for a validation set of particles including particles of any morphology as an input, and a PSD 804 for the validation set of particles as a verified output. The plurality of CLDs 801 are input into the model 803, and the model 803 subsequently outputs a PSD 804 based on the plurality of CLDs 801. Then, the PSD 804 output by the model is compared with the verified PSD 804 of the validation sample. Based on this comparison between the PSD 804 output by the model 803 and the verified PSD 804 of the validation sample, the model 803 is considered validated, and the model moves on to the testing phase, or the model 803 is not considered to be validated, and re-enters the training phase to undergo further training.

In alternative embodiments, the model 803 is not trained and validated as a single unit, but rather, each individual component of the model 803 is separately trained and separately validated. Specifically, in alternative embodiments, the morphology estimation model 907 and the universal morphology model 1301 are separately trained and validated using unique training and validation datasets, respectively. In such embodiments, the morphology estimation model 907 is trained and validated using its own training and validation dataset, respectively, and the universal morphology model 1301 is trained and validated using its own training and validation dataset, respectively.

Because the morphology estimation model 907 is configured to receive a plurality of CLDs 801 of different types for a set of particles including particles of any morphology, each training sample in the training dataset for the morphology estimation model 907 includes, as an input, a plurality of CLDs 801 of different types for a training set of particles including any morphology, and, as a verified output, a morphology for the training set of particles. As discussed above, in some embodiments, the morphology for the training set of particles comprises a plurality of morphologies for the set of particles, and each morphology of the plurality of morphologies is associated with a fraction that describes the proportion of particles of the set of particles that have the morphology. In some embodiments, each training sample in the training dataset also includes one or more of an in-line particle concentration and an in-line particle video as inputs. The plurality of CLDs 801, and in some embodiments one or more of the in-line particle concentration and the in-line particle video, are input into the morphology estimation model 907, and the morphology estimation model 907 subsequently outputs an estimated morphology 805 for the training set of particles based on the plurality of CLDs 801, and in some embodiments one or more of the in-line particle concentration and the in-line particle video. Then, the estimated morphology 805 output by the morphology estimation model 907 is compared with the verified morphology of the training sample. Based on this comparison between the estimated morphology 805 output by the morphology estimation model 907 and the verified morphology of the training sample, the parameters of the morphology estimation model 907 are modified to enable the morphology estimation model 907 to generate more accurate estimated particle morphologies 805 in future uses.

Similarly, in such embodiments in which the morphology estimation model 907 is validated as a single unit, each validation sample in the plurality of validation samples that includes the validation dataset includes, as an input, a plurality of CLDs 801 of different types for a validation set of particles including any morphology, and as a verified output, a morphology for the validation set of particles. In some embodiments, the morphology for the validation set of particles comprises a plurality of morphologies for the set of particles, and each morphology of the plurality of morphologies is associated with a fraction that describes the proportion of particles of the set of particles that have the morphology. In some embodiments, each validation sample in the validation dataset also includes one or more of an in-line particle concentration and an in-line particle video as inputs. The plurality of CLDs 801, and in some embodiments one or more of the in-line particle concentration and the in-line particle video, are input into the morphology estimation model 907, and the morphology estimation model 907 subsequently outputs an estimated morphology 805 based on the plurality of CLDs 801, and in some embodiments one or more of the inline particle concentration and the in-line particle video. Then, the estimated morphology 805 output by the model is compared with the verified morphology of the validation sample. Based on this comparison between the estimated morphology 805 output by the morphology estimation model 907 and the verified morphology of the validation sample, either the morphology estimation model 907 is considered validated, and the model moves on to the testing phase, or the morphology estimation model 907 is not considered to be validated, and re-enters the training phase to undergo further training.

The universal morphology model 1301 is configured to receive a plurality of CLDs 801 of different types for a set of particles including particles of any morphology, and an estimated morphology 805 for the set of particles. Thus each training sample in the training dataset for the universal morphology model 1301 includes, as inputs, a plurality of CLDs 801 of different types for a training set of particles including any morphology and a morphology for the training set of particles, and, as a verified output, a PSD 804 for the set of particles. The plurality of CLDs 801 as well as the morphology for the training set of particles are input into the universal morphology model 1301, and the universal morphology model 1301 subsequently outputs a PSD 804 based on the plurality of CLDs 801 and the morphology for the training set of particles. Then, the PSD 804 output by the universal morphology model 1301 is compared with the verified PSD 804 of the training sample. Based on this comparison between the PSD 804 output by the universal morphology model 1301 and the verified PSD 804 of the training sample, the parameters of the universal morphology model 1301 are modified to enable the universal morphology model 1301 to generate more accurate PSDs 804 in future uses.

Similarly, in such embodiments in which the universal morphology model 1301 is validated as a single unit, each validation sample in the plurality of validation samples that includes the validation dataset includes, as inputs, a plurality of CLDs 801 of different types for a validation set of particles including any morphology and a morphology for the validation set of particles, and as a verified output, a PSD 804 for the validation set of particles. The plurality of CLDs 801 and the morphology for the validation set of particles are input into the universal morphology model 1301, and the universal morphology model 1301 subsequently outputs a PSD 804 based on the plurality of CLDs 801 and the morphology. Then, the PSD 804 output by the model is compared with the verified PSD 804 of the validation sample. Based on this comparison between the PSD 804 output by the universal morphology model 1301 and the verified PSD 804 of the validation sample, either the universal morphology model 1301 is considered validated, and the model moves on to the testing phase, or the universal morphology model 1301 is not considered to be validated, and re-enters the training phase to undergo further training.

In embodiments in which the morphology estimation model 907 is trained and validated as a single unit, in general, the morphology estimation model 907 includes a function representing a relation between a plurality of CLDs 801 of different types for a set of particles and the morphology for the set of particles, the function based on a training dataset for the morphology estimation model 907.

FIG. 14 is a system diagram 1400 of the universal morphology model 1301 of FIG. 13, in accordance with an embodiment. As seen in FIG. 14, a plurality of CLDs 801 of different types for a set of particles, a morphology estimate 805 for the set of particles, and in some embodiments additional variables 802, are input into the universal morphology model 1301, and the universal morphology model 1301 subsequently outputs a PSD 804 for the set of particles. As discussed above with regard to FIG. 13, the universal morphology model 1301 is CLD type non-specific and particle morphology non-specific. In other words, the universal morphology model 1301 can determine a PSD 804 based on a plurality of CLDs 801 of different types and a morphology estimate 805, for a set of particles including particles of any morphology. This non-specificity of the universal morphology model 1301 to a single CLD type is illustrated in FIG. 14 by depicting a CLD 801 of each type as an input to the universal morphology model 1301. Specifically, FIG. 14 depicts a type A CLD 801A, a type B CLD 801B, a type C CLD 801C, and a type D CLD 801D, each being input into the universal morphology model 1301. Note that this illustration in FIG. 14 does not indicate that a CLD 801 of each type must be input into the universal morphology model 1301 to generate a PSD 804. Rather, this illustration in FIG. 14 indicates that any number of CLDs 801 of different types may be input into the universal morphology model 1301 to generate a PSD 804.

In the embodiment of the universal morphology model 1301 depicted in FIG. 14, the universal morphology model 1301 includes three separate, sequential components. Specifically, the universal morphology model 1301 includes a CLD descriptor identifier 908, a statistical model 909, and a parameterized PSD model 910.

Turning first to the CLD descriptor identifier 908, the CLD descriptor identifier 908 receives the plurality of CLDs 801 (in some embodiments a single CLD 801) and outputs a plurality of descriptors of the plurality of CLDs 801. In some embodiments, the plurality of descriptors of the plurality of CLDs 801 that are output by the CLD descriptor identifier 908 include one or more moments of the plurality of CLDs 801. In further embodiments, the plurality of descriptors of the plurality of CLDs 801 that are output by the CLD descriptor identifier 908 can also include a percentage of particles in the set of particles associated with the plurality of CLDs 801 that have a particle size below an average particle size.

Turning next to the statistical model 909, the statistical model 909 receives a plurality of descriptors of a plurality of CLDs 801 output by the CLD descriptor identifier 908, and a morphology estimate 805 output by the morphology estimation model 907. In some embodiments, the statistical model 909 also receives additional variables 802. The additional variables 802 can include, for example, a slurry concentration for the set of particles associated with the plurality of CLDs 801. The statistical model 909 then estimates metrics for the PSD 804 based on the plurality of identified descriptors of the plurality of CLDs 801 and the morphology estimate 805, and in some embodiments, the additional variables 802. In certain embodiments, the statistical model includes a regression model that is configured to perform regression analysis to estimate the metrics for the PSD 804.

Turning next to the parameterized PSD model 910, the parameterized PSD model 910 receives the PSD metrics output by the statistical model 909 and the morphology estimate 805 output by the morphology estimation model 907, and generates an estimate of the PSD 804 based on the PSD metrics and the morphology estimate 805. This estimate of the PSD 804 is subsequently output by the universal morphology model 1301. In some embodiments, the parameterized PSD model 910 includes a neural network model.

As discussed above with regard to FIG. 13, prior to using the universal morphology model 1301 for testing, the universal morphology model 1301 is trained and validated. In some embodiments, the universal morphology model 1301 is trained and validated as a single unit. Such embodiments are discussed above with regard to FIG. 13.

In alternative embodiments, the universal morphology model 1301 is not trained and validated as a single unit, but rather, each individual component of the universal morphology model 1301 is separately trained and separately validated. Specifically, in alternative embodiments, the CLD descriptor identifier 908, the statistical model 909, and the parameterized PSD model 910 are separately trained and validated using unique training and validation datasets, respectively. As discussed above, with regard to FIG. 13, because the universal morphology model 1301 is both CLD type and particle morphology non-specific, each training sample in the training dataset for each of the three components of the universal morphology model 1301, and each validation sample in the validation dataset for each of the three components of the universal morphology model 1301, can be based on a plurality of CLDs 801 of different types, for particles including any particle morphology, and on a morphology estimate 805 for the set of particles.

Each training sample in the plurality of training samples that includes the training dataset for the CLD descriptor identifier 908 includes a plurality of CLDs 801 of different types as an input and a plurality of descriptors of the plurality of CLDs 801 of different types as a verified output. The plurality of CLDs 801 are input into the CLD descriptor identifier 908, and the CLD descriptor identifier 908 subsequently outputs a plurality of descriptors based on the plurality of CLDs 801. Then, the plurality of descriptors output by the CLD descriptor identifier 908 is compared with the verified plurality of descriptors of the training sample. Based on this comparison between the plurality of descriptors output by the CLD descriptor identifier 908 and the verified plurality of descriptors of the training sample, the parameters of the CLD descriptor identifier 908 are modified to enable the CLD descriptor identifier 908 to generate more accurate descriptors in future uses.

Similarly, in such embodiments in which the CLD descriptor identifier 908 is validated as a single unit, each validation sample in the plurality of validation samples that includes the validation dataset includes a plurality of CLDs 801 of different types as an input and a plurality of descriptors as a verified output. The plurality of CLDs 801 are input into the CLD descriptor identifier 908, and the CLD descriptor identifier 908 subsequently outputs a plurality of descriptors based on the plurality of CLDs 801. Then, the plurality of descriptors output by the model is compared with the verified plurality of descriptors of the validation sample. Based on this comparison between the plurality of descriptors output by the CLD descriptor identifier 908 and the verified plurality of descriptors of the validation sample, either the CLD descriptor identifier 908 is considered validated, and the model moves on to the testing phase, or the CLD descriptor identifier 908 is not considered to be validated, and re-enters the training phase to undergo further training.

Each training sample in the plurality of training samples that is included in the training dataset for the statistical model 909, includes a plurality of descriptors of a plurality of CLDs 801 and a morphology for a training set of particles as inputs, and PSD metrics for a PSD 804 for the training set of particles as a verified output. In some embodiments, each training sample in the training dataset also includes a slurry concentration as an input. The plurality of CLD descriptors, the morphology, and in some embodiments the slurry concentration, are input into the statistical model 909, and the statistical model 909 subsequently outputs PSD metrics based on the plurality of descriptors, the morphology, and in some embodiments the slurry concentration. Then, the PSD metrics output by the statistical model 909 are compared with the verified PSD metrics of the training sample. Based on this comparison between the PSD metrics output by the statistical model 909 and the verified PSD metrics of the training sample, the parameters of the statistical model 909 are modified to enable the statistical model 909 to generate more accurate PSD metrics in future uses.

Similarly, in such embodiments in which the statistical model 909 is validated as a single unit, each validation sample in the plurality of validation samples that includes the validation dataset includes a plurality of descriptors of a plurality of CLDs 801 and a morphology for a validation set of particles as an input, and PSD metrics for a PSD 804 for the validation set of particles as a verified output. In some embodiments, each validation sample in the validation dataset also includes a slurry concentration as an input. The plurality of CLD descriptors, the morphology, and in some embodiments the slurry concentration, are input into the statistical model 909, and the statistical model 909 subsequently outputs PSD metrics based on the plurality of descriptors, the morphology, and in some embodiments the slurry concentration. Then, the PSD metrics output by the model are compared with the verified PSD metrics of the validation sample. Based on this comparison between the PSD metrics output by the statistical model 909 and the verified PSD metrics of the validation sample, either the statistical model 909 is considered validated, and the model moves on to the testing phase, or the statistical model 909 is not considered to be validated, and re-enters the training phase to undergo further training.

Similarly, for the parameterized PSD model 910, each training sample in the plurality of training samples that includes the training dataset for the parameterized PSD model 910 includes PSD metrics for a PSD 804 for a training set of particles and a morphology estimate for the training set of particles as inputs, and a PSD 804 for the training set of particles as a verified output. The PSD metrics and the morphology estimate are input into the parameterized PSD model 910, and the parameterized PSD model 910 subsequently outputs a PSD 804 based on the PSD metrics and the morphology estimate. Then, the PSD 804 output by the parameterized PSD model 910 is compared with the verified PSD 804 of the training sample. Based on this comparison between the PSD 804 output by the parameterized PSD model 910 and the verified PSD 804 of the training sample, the parameters of the parameterized PSD model 910 are modified to enable the parameterized PSD model 910 to generate a more accurate PSD 804 in future uses.

Similarly, in such embodiments in which the parameterized PSD model 910 is validated as a single unit, each validation sample in the plurality of validation samples that includes the validation dataset includes PSD metrics for a PSD 804 for a validation set of particles and the morphology estimate for the validation set of particles as inputs, and a PSD 804 for the validation set of particles as a verified output. The PSD metrics and the morphology estimate are input into the parameterized PSD model 910, and the parameterized PSD model 910 subsequently outputs a PSD 804 based on the PSD metrics and the morphology estimate. Then, the PSD 804 output by the model is compared with the verified PSD 804 of the validation sample. Based on this comparison between the PSD 804 output by the parameterized PSD model 910 and the verified PSD 804 of the validation sample, either the parameterized PSD model 910 is considered validated, and the model moves on to the testing phase, or the parameterized PSD model 910 is not considered to be validated, and re-enters the training phase to undergo further training.

In embodiments in which the statistical model 909 is trained and validated as a single unit, in general the statistical model 909 includes a function representing a relation between a plurality of identified descriptors for a plurality of CLDs 801, a morphology estimate, and PSD metrics for a PSD 804, the function based on a training dataset for the statistical model 802. Similarly, in embodiments in which the parameterized PSD model 910 is trained and validated as a single unit, in general the parameterized PSD model 910 includes a function representing a relation between PSD metrics for a PSD 804, a morphology estimate, and the PSD 804, the function based on a training dataset for the parameterized PSD model 910.

Figure 15:
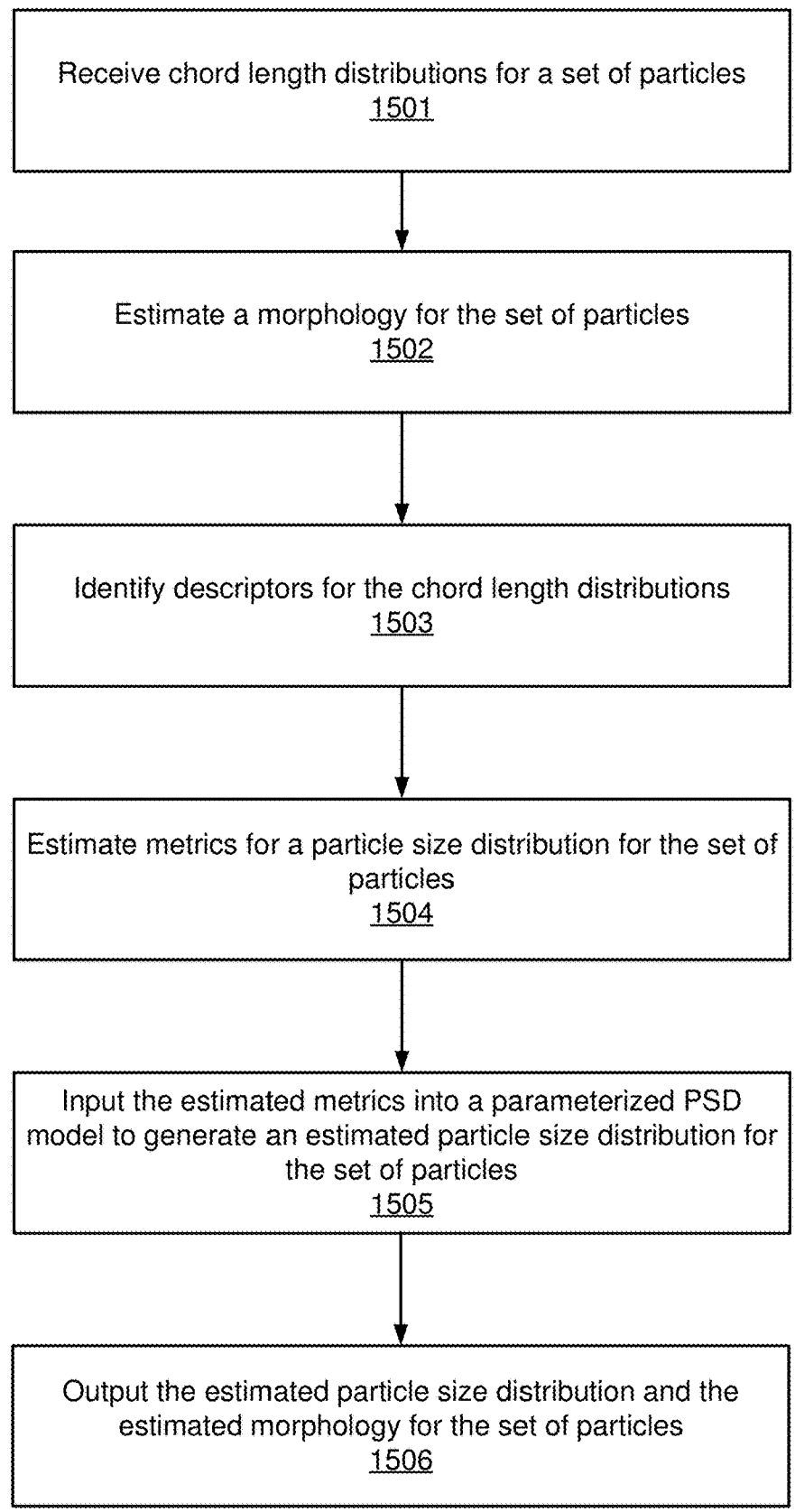
FIG. 15 is a flow chart of a method for generating a PSD and a morphology estimate for a set of particles, in accordance with an embodiment.

FIG. 15 is a flow chart of a method for generating a PSD and a morphology estimate for a set of particles, in accordance with an embodiment. In other embodiments, the method may include different and/or additional steps than those shown in FIG. 15. Additionally, steps of the method may be performed in different orders than the order described in conjunction with FIG. 15 in various embodiments.

A computer system receives 1501 plurality of CLDs of different types for a set of particles. In some embodiments, the plurality of CLDs are received from a probe, for example, the probe depicted in FIG. 1. The plurality of CLDs received by the computer system include different types CLDs. More specifically, the plurality of CLDs received by the computer system include any number of types of CLDs, referred to herein as CLD type A, CLD type B, CLD type C, and CLD type D.

The computer system estimates 1502 a morphology for the set of particles. In some embodiments, this estimation of a morphology for the set of particles is performed by a morphology estimation model, for example, the morphology estimation model discussed with regard to one or more of FIGS. 10-14. The morphology for the set of particles is estimated 1502 based on the plurality of CLDs for the set of particles that was received in step 1501.

The computer system identifies 1503 descriptors for the plurality of CLDs. In some embodiments, this identification of descriptors for the plurality of CLDs for the set of particles is performed by a descriptor identifier, for example, the descriptor identifier discussed with regard to one or more of FIGS. 5 and 10-14. The descriptors for the plurality of CLDs for the set of particles are identified 1503 based on the plurality of CLDs received in step 1501. In some embodiments, the descriptors for the plurality of CLDs for the set of particles are identified 1503 further based on the morphology for the set of particles estimated in step 1502. In alternative embodiments, the morphology for the set of particles is estimated 1502 based on the descriptors for the plurality of CLDs for the set of particles identified in step 1503.

The computer system estimates 1504 metrics for a PSD for the set of particles. In some embodiments, this identification of metrics for the PSD for the set of particles is performed by a statistical model, for example, the statistical model discussed with regard to one or more of FIGS. 5 and 10-14. The metrics for the PSD for the set of particles are estimated 1504 based on the descriptors of the plurality of CLDs for the set of particles identified in step 1503. In some embodiments, the metrics for the PSD for the set of particles are estimated 1504 further based on the morphology for the set of particles estimated in step 1502.

The computer system inputs 1505 the estimated metrics for the PSD for the set of particles into a parameterized PSD model to generate an estimated PSD for the set of particles. In some embodiments, the parameterized PSD model is the parameterized PSD model discussed with regard to one or more of FIGS. 5-6 and 10-14. In some embodiments, the PSD for the set of particles is estimated 1504 further based on the morphology for the set of particles estimated in step 1502.

The computer system outputs 1506 the estimated PSD and the estimated morphology for the set of particles.

System Architecture: Dominant Particle Formation Mechanism Identification

As discussed above with regard to FIGS. 7A-E, a set of particles may transform according to one or more dominant particle formation mechanisms. For example, in some embodiments, dominant particle formation mechanisms may cause particles in a set of particles to change morphology. In some embodiments, it may be desirable for a model to be capable of identifying one or more dominant particle formation mechanisms that have affected one or more particles in a set of particles. Models with such capabilities are discussed in detail herein with regard to FIGS. 16-19.

Figure 16:
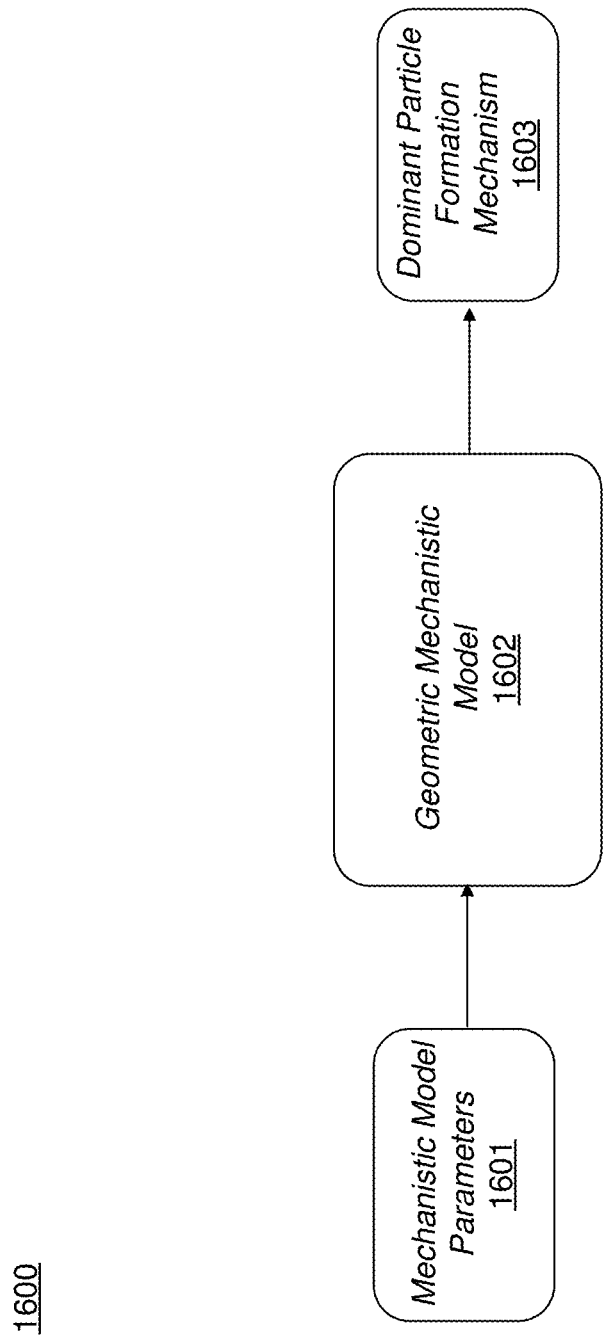
FIG. 16 is a system diagram of a system for identifying a dominant particle formation mechanism for a set of particles, in accordance with an embodiment.

FIG. 16 is a system diagram 1600 of a system for identifying a dominant particle formation mechanism 1603 for a set of particles, in accordance with an embodiment. In the embodiment depicted in FIG. 16, a geometric mechanistic model 1602 receives mechanistic model parameters 1601 for a set of particles, and identifies a dominant particle formation mechanism 1603 for the set of particles. The dominant particle formation mechanism 1603 is a qualitative property.

The mechanistic model parameters 1601 for the set of particles include parameters that have been optimized to fit experimental data for the set of particles. The geometric mechanistic model 1602 is a theoretical model that is configured to generate a theoretical CLD for a set of particles, based on the mechanistic model parameters 1601 received for the set of particles. Based on this theoretical CLD generated by the geometric mechanistic model 1602, the geometric mechanistic model 1602 then identifies a dominant particle formation mechanism 1603 for the set of particles.

However, in its generation of the theoretical CLD, the geometric mechanistic model 1602 may ignore much of the underlying physics. Therefore, the theoretical CLD generated by the geometric mechanistic model 1602, and thus the dominant particle formation mechanism 1603 identified based on the theoretical CLD, can be inaccurate. Due to this inaccuracy in identification of the dominant particle formation mechanism 1603 by the geometric mechanistic model 1602, it is desirable to configure an alternative model to more accurately identify one or more dominant particle formation mechanisms 1603 that have affected one or more particles in a set of particles. One such model is discussed in detail below with regard to FIGS. 17-18.

Figure 17:
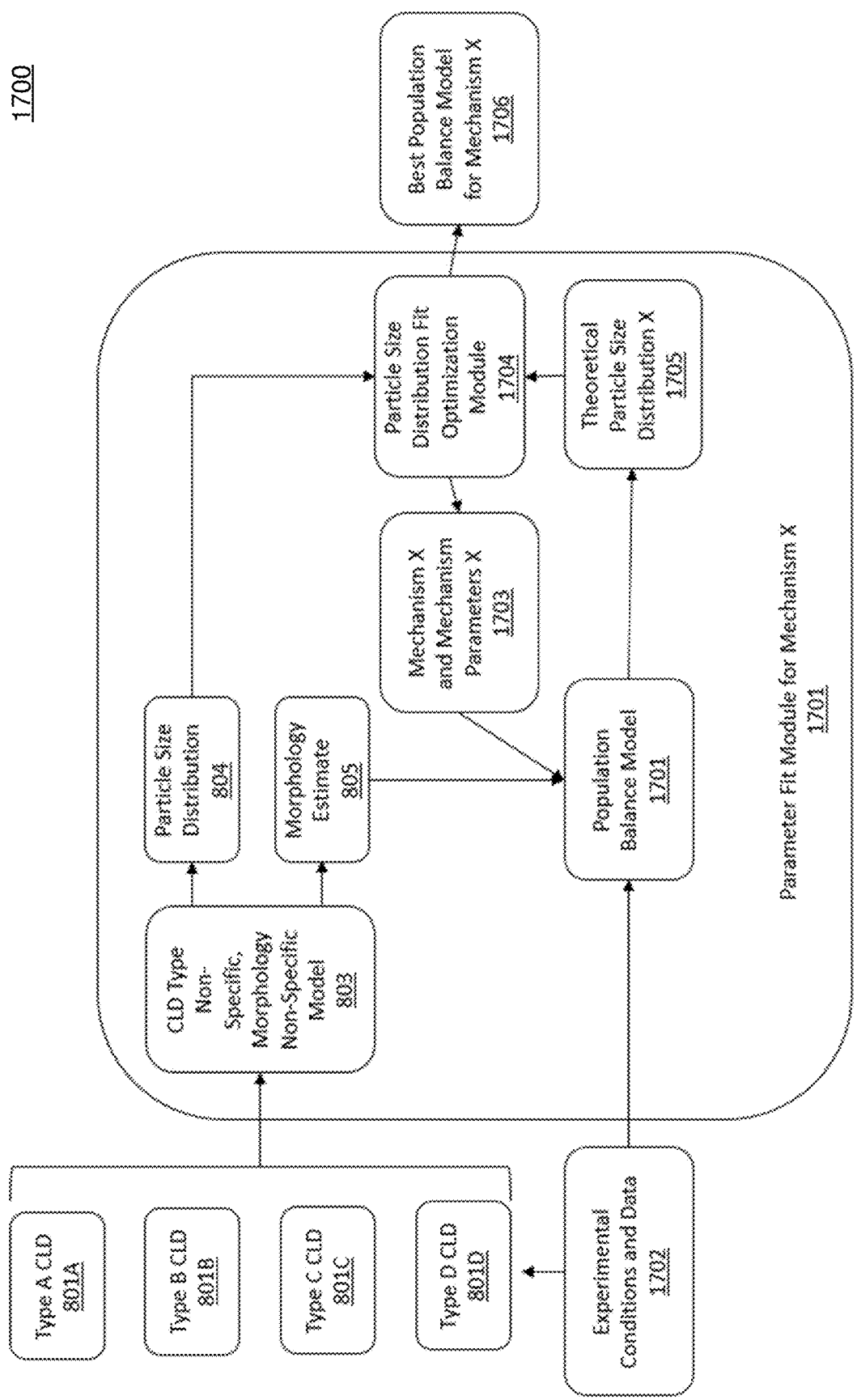
FIG. 17 is a system diagram of a system for identifying the best population balance model for a given formation mechanism for a set of particles, in accordance with an embodiment.
Figure 18:
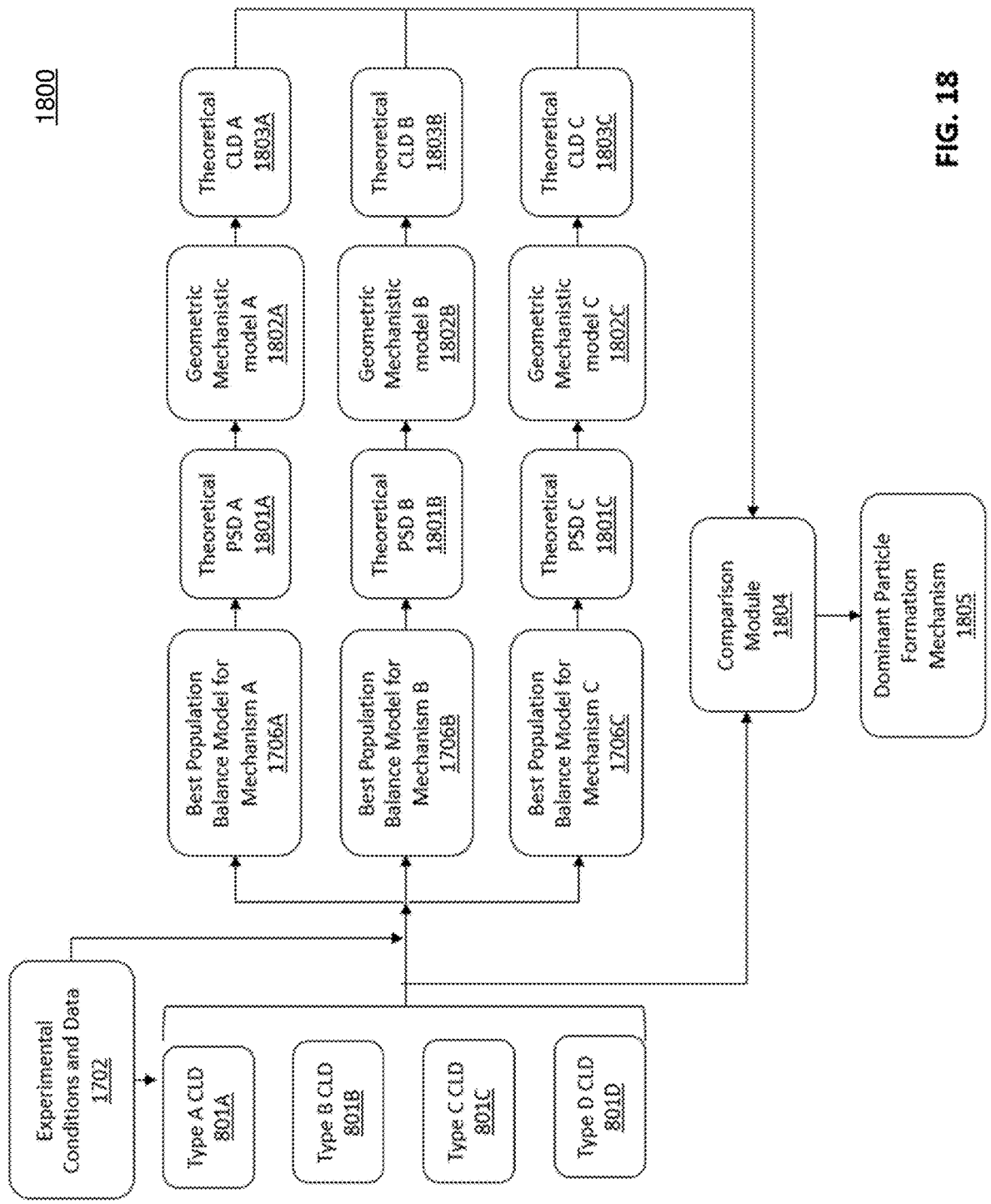
FIG. 18 is a system diagram of a system for identifying a dominant particle formation mechanism for a set of particles based on the best population balance models identified for different mechanisms, in accordance with an embodiment.

FIGS. 17-18 are system diagrams 1700 and 1800 of a system for identifying a dominant particle formation mechanism 1805 for a set of particles, in accordance with an embodiment. Specifically, as discussed in detail below, the system depicted in FIGS. 17-18 identifies a dominant particle formation mechanism 1805 for a set of particles by identifying a best population balance model 1706 for each potential dominant particle formation mechanism for the set of particles, and comparing the outputs of the best population balance models 1706 for the potential dominant particle formation mechanisms to identify a dominant particle formation mechanism 1805 that best fits the set of particles.

Turning first to FIG. 17, the system uses an embodiment of the model 803 discussed above with regard to FIGS. 9-15. Specifically, the system uses the first embodiment of the model 803 discussed above with regard to FIGS. 10-12, the second embodiment of the model 803 discussed above with regard to FIGS. 13-14, and/or an alternative embodiment of the model 803 not explicitly discussed herein.

As discussed above with regard to FIGS. 9-15, the model 803 is both CLD type and morphology non-specific. This non-specificity of the model 803 to a single CLD type is illustrated in FIG. 17 by depicting a CLD of each type as an input to the model 803. Specifically, FIG. 17 depicts a type A CLD 801A, a type B CLD 801B, a type C CLD 801C, and a type D CLD 801D, each being input into the model 803. Note that this illustration in FIG. 17 does not indicate that a CLD 801 of each type must be input into the model 803. Rather, this illustration in FIG. 17 indicates that any number of CLDs 801 of different types may be input into the model 803.

Based on the plurality of CLDs 801 of different types input into the model 803, the model 803 generates a PSD 804 and a morphology estimate 805 according to one or more of the embodiments described above with regard to FIGS. 9-15. Then, the PSD 804 is input into a particle size distribution fit optimization module 1704. The particle size distribution fit optimization module 1704 identifies a dominant particle formation mechanism X and dominant particle formation mechanism parameters 1703 for the dominant particle formation mechanism X for the set of particles.

Then the identified dominant particle formation mechanism parameters 1703 for the dominant particle formation mechanism X for the set of particles, the morphology estimate 805, and experimental conditions and data 1702, are input into a population balance model (PBM) 1701 that is associated with the dominant particle formation mechanism X. In general, a PBM is a mechanistic model that is associated with a dominant particle formation mechanism, and is configured to generate a theoretical particle size distribution for a set of particles with the associated dominant particle formation mechanism. Accordingly, the PBM 1701 outputs a theoretical particle size distribution 1705 for the set of particles with the dominant particle formation mechanism X. In some embodiments, the PBM 1701 also outputs a solute concentration in addition to the theoretical particle size distribution 1705.

The theoretical particle size distribution 1705, and in some embodiments the solute concentration, generated by the PBM 1701 are input into the particle size distribution fit optimization module 1704. The particle size distribution fit optimization module 1704 modifies the dominant particle formation mechanism parameters 1703 for the dominant particle formation mechanism X for the set of particles by reducing the differences between the theoretical particle size distribution 1705 and the particle size distribution 804. Based on this reduction, a best population balance model, including the modified parameters, for the dominant particle formation mechanism X 1706 is identified.

The process discussed above with regard to FIG. 17 is performed for a plurality of potential dominant particle formation mechanisms X. The result is a plurality of best population balance models 1706, one for each of the plurality of potential dominant particle formation mechanisms X. To identify the most likely dominant particle formation mechanism X from the plurality of potential dominant particle formation mechanisms X, for each best population balance model 1706 associated with a potential dominant particle formation mechanism X, the steps described below with regard to FIG. 18 are performed.

Specifically, as seen in FIG. 18, each best population balance model 1706 associated with a potential dominant particle formation mechanism X generates a theoretical PSD 1801 based on CLDs 801A-D and based on the experimental conditions and data 1702. The theoretical PSD 1801 output by each PBM 1706 is input into a geometric mechanistic model 1802. Specifically, as seen in FIG. 18, the theoretical PSD A 1801A output by the PBM model A 1706A is input into a geometric mechanistic model A 1802A, the theoretical PSD B 1801B output by the PBM model B 1706B is input into a geometric mechanistic model B 1802B, and the theoretical PSD C 1801C output by the PBM model C 1706C is input into a geometric mechanistic model C 1802C.

As discussed above with regard to FIG. 16, a geometric mechanistic model 1802 is a theoretical model that is configured to generate a theoretical CLD for a set of particles, based on a received PSD. Therefore, each geometric mechanistic model 1802 generates a theoretical CLD 1803 for the set of particles. Specifically, as seen in FIG. 18, the geometric mechanistic model A 1802A generates a theoretical CLD A 1803A, the geometric mechanistic model B 1802B generates a theoretical CLD B 1803B, and the geometric mechanistic model C 1802C generates a theoretical CLD C 1803C.

The theoretical CLDs 1803 generated by the geometric mechanistic models 1802 are then each compared to the plurality of CLDs 801 that were originally input into the model 803, by a comparison module 1804. Specifically, the comparison module 1804 identifies the theoretical CLD 1803 that best matches the plurality of CLDs 801. In other words, the comparison module 1804 identifies the best fitting theoretical CLD 1803. In one embodiment, the best match is determined by looking at general trends of the theoretical CLD 1803 over time as compared to the general trend of the CLDs 801. For example, whether the theoretical CLD 1803 increases and decreases at same times as the CLDs 801 and whether the rate of change is increasing or decreasing. These general trends may provide a better indication of which particle formation mechanism is primarily driving the observed changes in CLD due to the inaccuracies in the raw values calculated for the theoretical CLD 1803.

Based on the best fitting theoretical CLD 1803 identified by the comparison module 1804, the best fitting PBM is identified from the set of PBMs 1706. Specifically, the PBM 1706 that generated the best fitting theoretical CLD 1803 is identified by the comparison module 1804 as the best fitting PBM.

Finally, the PBM 1706 identified as the best fitting PBM is used to identify a dominant particle formation mechanism 1805 for the set of particles. Specifically, the dominant particle formation mechanism associated with the best fitting PBM is identified as the dominant particle formation mechanism 1805.

Figure 19:
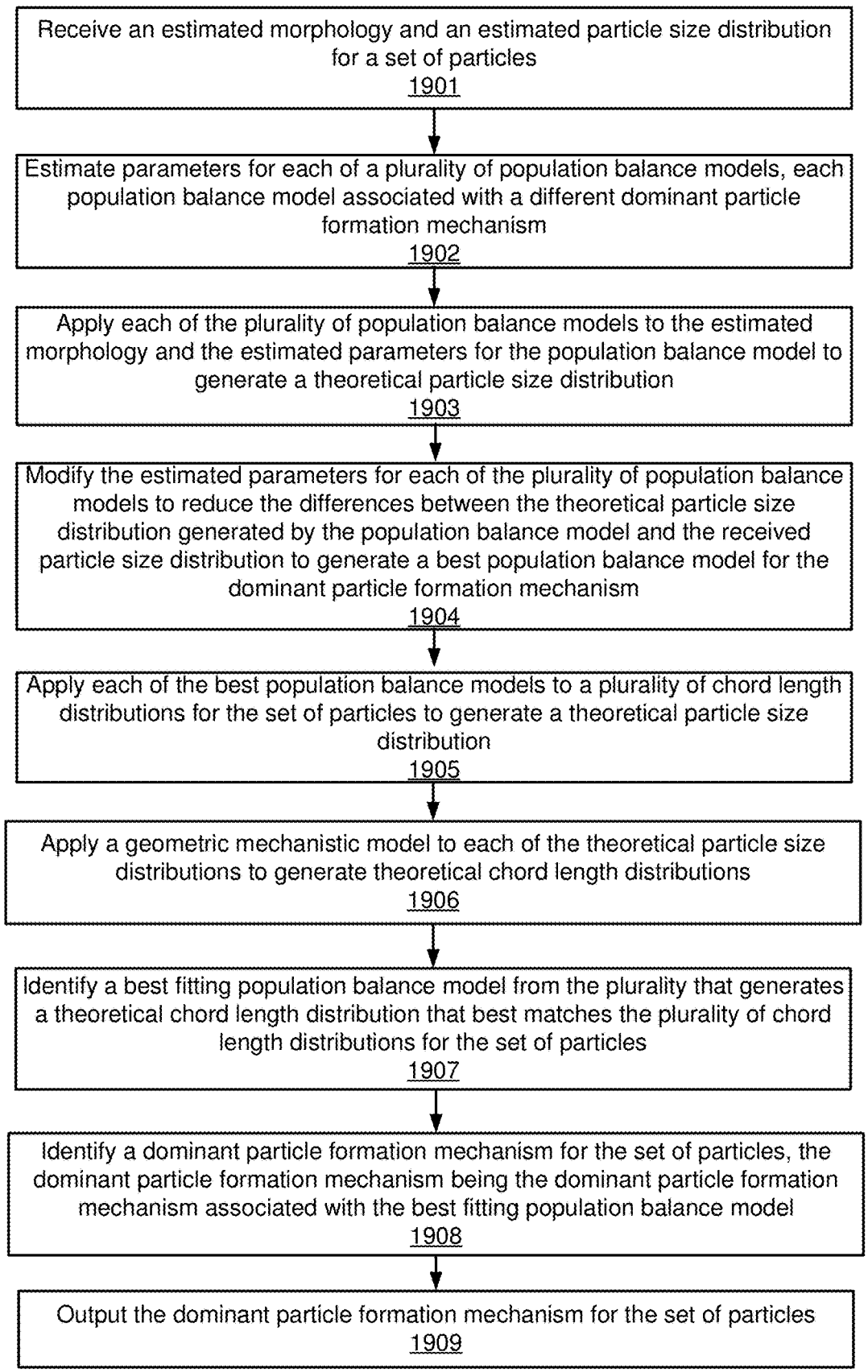
FIG. 19 is a flow chart of a method for identifying a dominant particle formation mechanism for a set of particles, in accordance with an embodiment.

FIG. 19 is a flow chart of a method for identifying a dominant particle formation mechanism for a set of particles, in accordance with an embodiment. In other embodiments, the method may include different and/or additional steps than those shown in FIG. 19. Additionally, steps of the method may be performed in different orders than the order described in conjunction with FIG. 19 in various embodiments.

A computer system receives 1901 an estimated morphology and an estimated PSD for a set of particles. In some embodiments, the estimated morphology and the estimated PSD are generated by an embodiment of the model described above with regard to FIGS. 9-15. As described above with regard to FIGS. 9-15, the estimated morphology and the estimated PSD for the set of particles may be based on a plurality of CLDs of different types for the set of particles, the set of particles including particles of any morphology.

The computer system estimates 1902 parameters for each of a plurality of PBMs, each PBM associated with a different dominant particle formation mechanism. The parameters for each PBM are based on the estimated PSD for the set of particles, as received in step 1901.

The computer system applies 1903 each of the plurality of PBMs to the morphology estimate 805 and the parameters estimated for the PBM in step 1902 to generate theoretical PSDs for the set of particles.

The computer system modifies 1904 the parameters estimated for each of the plurality of PBMs to reduce the differences between the theoretical PSD generated by the PBM and the PSD received in step 1901 to generate a best PBM for the dominant particle formation mechanism.

The computer system applies 1905 each of the best PBMs generated in step 1906 to a plurality of CLDs for the set of particles to generate theoretical PSDs.

The computer system applies 1906 a geometric mechanistic model to the theoretical PSD generated by each of the best PBMs in step 1905 to generate theoretical CLDs.

The computer system identifies 1907 a best fitting PBM from the plurality of PBMs that generates a theoretical CLD that best matches the plurality of CLDs for the set of particles. Specifically, the theoretical CLDs generated by the geometric mechanistic model are each compared to the plurality of CLDs for the set of particles. Based on this comparison, the theoretical CLD that most closely matches the plurality of CLDs is identified. In other words, the best fitting theoretical CLD is identified. Then, the PBM that generated the best fitting theoretical CLD is identified as the best fitting PBM.

The computer system identifies 1908 a dominant particle formation mechanism for the set of particles, the dominant particle formation mechanism being the dominant particle formation mechanism associated with the best fitting PBM identified in step 1907.

The computer system outputs 1909 the dominant particle formation mechanism for the set of particles. In this way, the most accurate dominant particle formation mechanism can be identified for the set of particles.

System Architecture: Computer System

Figure 20:
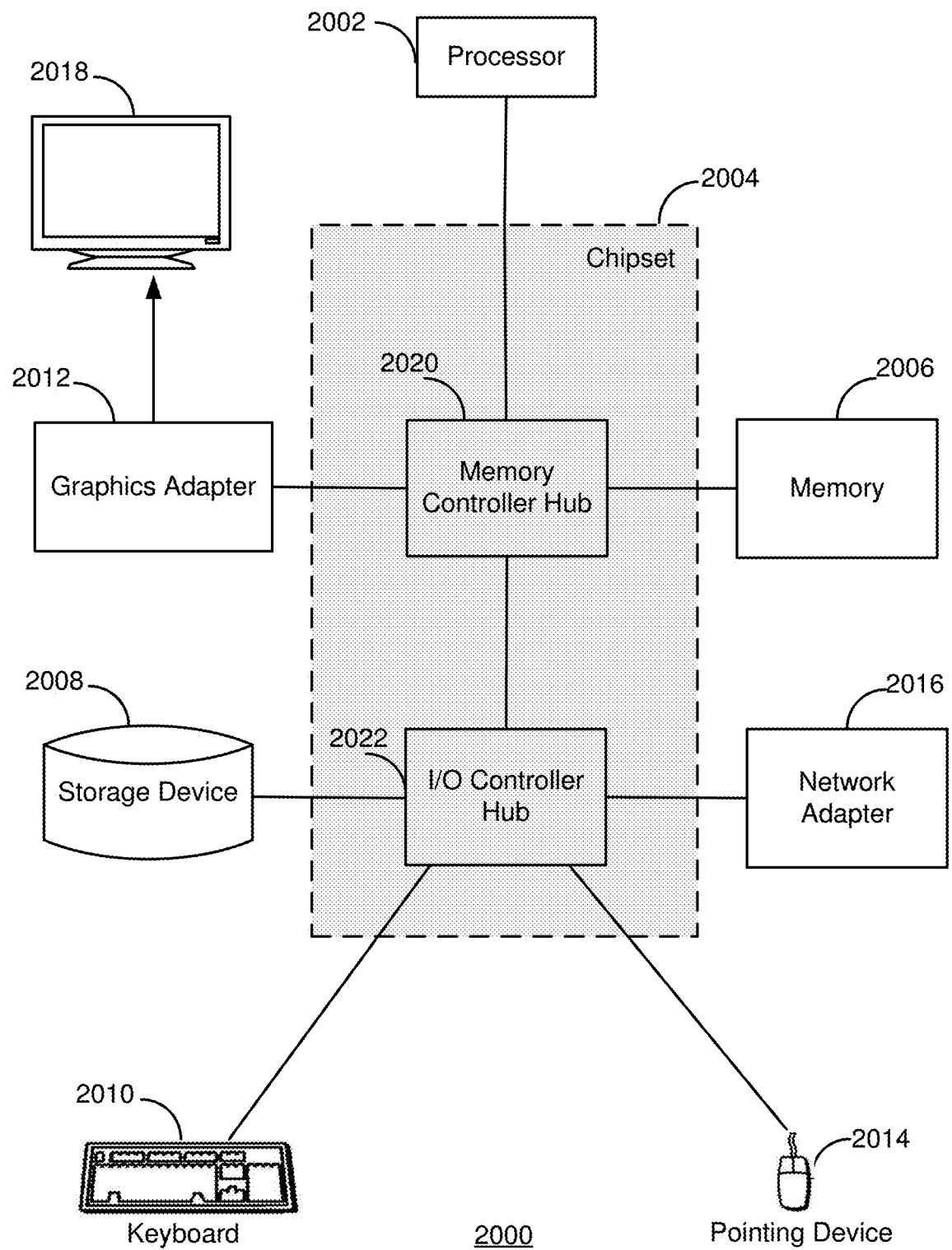
FIG. 20 illustrates an example computer for implementing the methods described with regard to FIGS. 1-18, in accordance with an embodiment.

FIG. 20 illustrates an example computer 2000 for implementing the methods described with regard to FIGS. 1-19, in accordance with an embodiment. The computer 2000 includes at least one processor 2002 coupled to a chipset 2004. The chipset 2004 includes a memory controller hub 2020 and an input/output (I/O) controller hub 2022. A memory 2006 and a graphics adapter 2012 are coupled to the memory controller hub 2020, and a display 2018 is coupled to the graphics adapter 2012. A storage device 2008, an input device 2014, and network adapter 2016 are coupled to the I/O controller hub 2022. Other embodiments of the computer 2000 have different architectures.

The storage device 2008 is a non-transitory computer-readable storage medium such as a hard drive, compact disk read-only memory (CD-ROM), DVD, or a solid-state memory device. The memory 2006 holds instructions and data used by the processor 2002. The input interface 2014 is a touch-screen interface, a mouse, track ball, or other type of pointing device, a keyboard, or some combination thereof, and is used to input data into the computer 2000. In some embodiments, the computer 2000 may be configured to receive input (e.g., commands) from the input interface 2014 via gestures from the user. The graphics adapter 2012 displays images and other information on the display 2018. The network adapter 2016 couples the computer 2000 to one or more computer networks.

The computer 2000 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 2008, loaded into the memory 2006, and executed by the processor 2002.

The types of computers 2000 used to execute the methods of FIGS. 1-19 can vary depending upon the embodiment and the processing power required by the entity. For example, the particle classification system 900 depicted in FIG. 9 can run in a single computer 2000 or multiple computers 2000 communicating with each other through a network such as in a server farm. The computers 2000 can lack some of the components described above, such as graphics adapters 2012, and displays 2018.

What is claimed is:

1. A method for estimating a particle size distribution and a morphology for a set of particles, the method comprising:
    generating, from data generated by a probe interacting with the set of particles, a plurality of different chord length distributions for the set of particles, each of the plurality of different chord length distributions being of a different type, wherein each of the plurality of different chord length distributions is generated by processing and/or weighting the data generated by the probe differently;

receiving, at a computer system, the plurality of different chord length distributions of different types for the set of particles;

providing, by the computer system, all of the plurality of different chord length distributions as input to a morphology estimation model, the morphology estimation model outputting an estimate of a morphology of the set of particles;

identifying, by a descriptor identifier, based on the plurality of different chord length distributions for the set of particles, a plurality of descriptors of the plurality of different chord length distributions for the set of particles;

applying a statistical model, based on the plurality of identified descriptors of the plurality of different chord length distributions for the set of particles, to estimate metrics for the particle size distribution for the set of particles;

generating, by the computer system, an estimate of the particle size distribution for the set of particles by applying a parameterized PSD model to the metrics for the particle size distribution for the set of particles; and outputting, by the computer system, the estimated particle size distribution for the set of particles and the estimated morphology for the set of particles.

2. The method of claim 1, wherein the plurality of identified descriptors of the plurality of different chord length distributions for the set of particles comprises one or more of moments of the plurality of different chord length distributions or a percentage of particles in the set of particles with a particle size below an average particle size.

3. The method of claim 1, wherein the estimated morphology for the set of particles is further based on one or more of an in-line particle concentration for the set of particles or an in-line particle video for the set of particles.

4. The method of claim 1, wherein the morphology estimation model comprises one of a fuzzy classification model, a neuro-fuzzy classification model, a random forest model, a decision tree, a clustering algorithm, a neural network, a multi-class logistic regression model, a deep learning model, and a Bayesian model.

5. The method of claim 1, wherein, prior to estimating the morphology for the set of particles, the morphology estimation model is trained using a training dataset, the training dataset comprising a plurality of training samples, each training sample of the plurality of training samples associated with a training set of particles and comprising a plurality of training chord length distributions for the training set of particles, each training chord length distribution of the plurality comprising a different type of chord length distribution, and a morphology for the training set of particles, the training samples of the training dataset associated with training sets of particles comprising a plurality of different morphologies.

6. The method of claim 5, wherein each training sample of the training dataset further comprises one or more of an in-line particle concentration for the training set of particles and an in-line particle video for the training set of particles.

7. The method of claim 1, wherein the estimated metrics for the particle size distribution for the set of particles are further based on a slurry concentration of the set of particles.

8. The method of claim 1, wherein the statistical model comprises a regression model configured to perform regression analysis.

9. The method of claim 1, wherein, prior to estimating the metrics for the particle size distribution for the set of particles, the statistical model is trained using a training dataset, the training dataset comprising a plurality of training samples, each training sample of the plurality of training samples associated with a training set of particles and comprising descriptors of a plurality of training chord length distributions for the training set of particles, each training chord length distribution of the plurality comprising a different type of chord length distribution, and metrics for a particle size distribution for the training set of particles, the training samples of the training dataset associated with training sets of particles comprising a plurality of different morphologies.

10. The method of claim 1, wherein, prior to estimating the particle size distribution for the set of particles, the parameterized PSD model is trained using a training dataset, the training dataset comprising a plurality of training samples, each training sample of the plurality of training samples associated with a training set of particles and comprising particle size distribution metrics for the training set of particles and a particle size distribution for the training set of particles, the training samples of the training dataset associated with training sets of particles comprising a plurality of different morphologies.

11. The method of claim 1, wherein the descriptor identifier comprises a plurality of descriptor identifiers, each descriptor identifier of the plurality of descriptor identifiers associated with a different particle morphology, wherein the statistical model comprises a plurality of statistical models, each statistical model of the plurality of statistical models associated with a different particle morphology, wherein the parameterized PSD model comprises a plurality of parameterized PSD models, each parameterized PSD model of the plurality of parameterized PSD models associated with a different particle morphology, and wherein the method further comprises:

selecting, by the computer system, for identifying the plurality of descriptors of the plurality of different chord length distributions for the set of particles, a descriptor identifier from the plurality of descriptor identifiers that is associated with the estimated morphology for the set of particles;

selecting, by the computer system, for estimating the metrics for the particle size distribution for the set of particles, a statistical model from the plurality of statistical models that is associated with the estimated morphology for the set of particles; and selecting, by the computer system, for generating the estimated particle size distribution for the set of particles, a parameterized PSD model from the plurality of parameterized PSD models that is associated with the estimated morphology for the set of particles.

12. The method of claim 11, wherein, prior to estimating the metrics for the particle size distribution for the set of particles, each statistical model of the plurality of statistical models is trained using a training dataset comprising a plurality of training samples, each training sample associated with a training set of particles comprising the morphology associated with the statistical model and comprising descriptors of a plurality of training chord length distributions for the training set of particles, each training chord length distribution of the plurality comprising a different type of chord length distribution, and metrics for a particle size distribution for the training set of particles.

13. The method of claim 11, wherein, prior to estimating the particle size distribution for the set of particles, each parameterized PSD model of the plurality of parameterized PSD models is trained using a training dataset comprising a plurality of training samples, each training sample associated with a training set of particles comprising the morphology associated with the parameterized PSD model and comprising particle size distribution metrics for the training set of particles and a particle size distribution for the training set of particles.

14. The method of claim 1, wherein the estimated morphology for the set of particles is further based on the identified plurality of descriptors of the plurality of different chord length distributions for the set of particles.

15. The method of claim 1, wherein the parameterized PSD model comprises a function representing a relation between the estimated metrics for the particle size distribution for the set of particles and the estimated particle size distribution for the set of particles, and wherein the function is based on a training dataset for the parameterized PSD model.

16. The method of claim 1, wherein the statistical model comprises a function representing a relation between the plurality of identified descriptors for the plurality of different chord length distributions for the set of particles and the estimated metrics for the particle size distribution for the set of particles, and wherein the function is based on a training dataset for the statistical model.

17. The method of claim 1, wherein the estimated particle size distribution for the set of particles is further based on the estimated morphology for the set of particles.

18. The method of claim 17, wherein the estimated morphology for the set of particles comprises a plurality of estimated morphologies for the set of particles, each estimated morphology of the plurality of estimated morphologies associated with a fraction that describes the proportion of particles of the set of particles that have the estimated morphology.

19. The method of claim 11, wherein the selected descriptor identifier identifies the plurality of descriptors for one chord length distribution of the plurality of different chord length distributions and the selected statistical model estimates the metrics for the particle size distribution for the set of particles based on the plurality of descriptors for the one chord length distribution of the plurality of different chord length distributions.

20. The method of claim 1, wherein the plurality of different chord length distributions comprises four different chord length distributions.

* * * * *